United States Patent
Li et al.

(10) Patent No.: US 9,493,453 B2
(45) Date of Patent: Nov. 15, 2016

(54) PIPERAZINYL PYRIMIDINE DERIVATIVES, PREPARATION METHOD AND USE THEREOF

(71) Applicants: INSTITUTE OF PHARMACOLOGY AND TOXICOLOGY ACADEMY OF MILITARY MEDICAL SCIENCES P.L.A. CHINA, Beijing (CN); PEKING UNIVERSITY, Beijing (CN)

(72) Inventors: Song Li, Beijing (CN); Ying Wang, Beijing (CN); Junhai Xiao, Beijing (CN); Dalong Ma, Beijing (CN); Hongwei Gong, Beijing (CN); Hui Qi, Beijing (CN); Lili Wang, Beijing (CN); Xiaomei Ling, Beijing (CN); Zhibing Zheng, Beijing (CN); Yang Zhang, Beijing (CN); Wu Zhong, Beijing (CN); Meina Li, Beijing (CN); Yunde Xie, Beijing (CN); Enquan Xu, Beijing (CN); Xingzhou Li, Beijing (CN); Jing Ma, Beijing (CN); Guoming Zhao, Beijing (CN); Xinbo Zhou, Beijing (CN); Xiaokui Wang, Beijing (CN); Hongying Liu, Beijing (CN)

(73) Assignees: The Institute of Pharmacology and Toxicology Academy of Military Medical Science P.L.A. CHINA, Beijing (CN); PEKING UNIVERSITY, Beijing (CN)

( * ) Notice: Subject to any disclaimer, the term of this patent is extended or adjusted under 35 U.S.C. 154(b) by 34 days.

(21) Appl. No.: 14/372,710

(22) PCT Filed: Jan. 15, 2013

(86) PCT No.: PCT/CN2013/070469
§ 371 (c)(1),
(2) Date: Jul. 16, 2014

(87) PCT Pub. No.: WO2013/107333
PCT Pub. Date: Jul. 25, 2013

(65) Prior Publication Data
US 2015/0126500 A1 May 7, 2015

(30) Foreign Application Priority Data
Jan. 16, 2012 (CN) .......................... 2012 1 0011263

(51) Int. Cl.
| | |
|---|---|
| C07D 401/12 | (2006.01) |
| C07D 417/12 | (2006.01) |
| A61K 31/496 | (2006.01) |
| A61K 31/541 | (2006.01) |
| C07D 471/04 | (2006.01) |
| C07D 403/14 | (2006.01) |
| C07D 403/12 | (2006.01) |
| C07D 239/50 | (2006.01) |
| A61K 31/519 | (2006.01) |

(52) U.S. Cl.
CPC ............ C07D 471/04 (2013.01); C07D 239/50 (2013.01); C07D 401/12 (2013.01); C07D 403/12 (2013.01); C07D 403/14 (2013.01); C07D 417/12 (2013.01)

(58) Field of Classification Search
None
See application file for complete search history.

(56) References Cited

U.S. PATENT DOCUMENTS

| | | |
|---|---|---|
| 4,535,080 A | 8/1985 | Audiau et al. |
| 4,885,296 A | 12/1989 | Manoury et al. |
| 2009/0182140 A1 | 7/2009 | Furukubo et al. |

FOREIGN PATENT DOCUMENTS

| | | |
|---|---|---|
| CN | 101914142 A | 12/2010 |
| DE | 2341925 A1 | 3/1975 |
| EP | 1970373 A1 | 9/2008 |
| JP | 62-142177 | 6/1987 |
| TW | 200732336 A | 9/2007 |
| WO | 02/45652 A2 | 6/2002 |
| WO | 2004020584 A2 | 3/2004 |
| WO | 2005039587 A1 | 5/2005 |
| WO | 2005082865 A1 | 9/2005 |
| WO | 2005085212 A1 | 9/2005 |

(Continued)

OTHER PUBLICATIONS

Gong et al.Chemical Journal of Chinese Universities, 34(9), pp. 2131-2138 (Aug. 30, 2013).*
Zu et al. Molecules 2014, 19, 3539-3551.*
Sisko et al. Bioorganic & Medicinal Chemistry Letters 16 (2006) 1146-1150.*
CA Registry Nos. 1269359-44-5, 1269382-14-0 and 1269389-43-6 entered into the CA Registry File on Mar. 21, 2011, suppled by ChemBridge Corporation.*
ChemBridge Product Guide, 2 pages, retrieved from the Internet at http://www.chembridge.com/screening_libraries/ on Aug. 9, 2015.*

(Continued)

*Primary Examiner* — Emily Bernhardt
(74) *Attorney, Agent, or Firm* — Banner & Witcoff, Ltd.

(57) ABSTRACT

Provided are piperazinyl pyrimidine derivatives of formula I having $CCR_4$ antagonism, and the preparation method, pharmaceutical composition and use thereof in the preparation of a medicament. The medicament is useful for the treatment and prevention of $CCR_4$-related diseases.

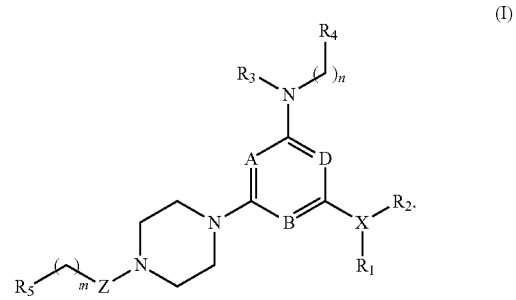

9 Claims, No Drawings

(56) References Cited

FOREIGN PATENT DOCUMENTS

| WO | 2006138304 A2 | 12/2006 |
| WO | 2009131598 A1 | 10/2009 |

OTHER PUBLICATIONS

International Search Report mailed Apr. 25, 2013 (PCT/CN2013/070469); ISA/CN.

May 5, 2015—(EPO) Extended European Search Report—App. 13 738 361.8.

Office Action and Search Report for CN201210011263.3 dated Jul. 10, 2014 with English translation, 21 pages.

Sanmartin et al., "Synthesis and biological evaluation of new symmetrical derivatives as cytotoxic agents and apoptosis inducers," Bioorganic & Medicinal Chemistry, vol. 13, pp. 2031-2044, 2005.

Ho et al, "Triazine and pyrimidine based ROCK inhibitors with efficacy in spontaneous hypertensive rat model," Bioorganic & Medicinal Chemistry Letters 19, 2009, pp. 6027-6031.

Huang et al., "Discovery of novel purine derivatives with potent and selective inhibitory activity against c-Src tyrosine kinase," Bioorganic & Medicinal Chemistry 18, 2010, pp. 4615-4624.

Sisko et al., "Potent 2-[(pyrimidin-4-yl)amine]-1,3-thiazole-5-carbonitrile-based inhibitors of VEGFR-2 (KDR) kinase," Bioorganic & Medicinal Chemistry Letters, 16 (2006) pp. 1146-1150.

* cited by examiner

PIPERAZINYL PYRIMIDINE DERIVATIVES, PREPARATION METHOD AND USE THEREOF

TECHNICAL FIELD

The present invention relates to novel piperazinyl pyrimidine derivatives capable of antagonizing human chemokine receptor 4 (hereinafter referred to as $hCCR_4$), the method of preparing the compounds, the pharmaceutical compositions comprising the compounds and the use of the compounds in the manufacture of a medicament for the treatment and/or prevention of $hCCR_4$-mediated diseases or disorders.

BACKGROUND ART $CCR_4$ (Chemokine Receptor 4) was first discovered in 1995 by Christine A. Power et al (Christine A. P. et al, J. Biol. Chem., 1995, 270 (8):19495-19500), which is one of members in chemokine receptor (CCR) family, and is a seven-transmembrane G-protein coupled receptor. It has two naturally occurring specific ligands: MDC (Macrophage-derive chemokine) and TARC (thymus and activation regulated chemokine) (Sadatoshi Maeda et al, Veterinary Immunology and Immunopathology 2002 (90): 145-154). The newly discovered chemokine-like factor 1 (Chemokine-like factor 1, CKLF1) is also one of its ligands (Han W. L. et al, Biochem. J., 2001, 357 (Pt1): 127-135).

$CCR_4$ can be expressed in peripheral blood leukocytes, thymus cells, basophils, monocytes, macrophages, platelets, IL-activated NK cells, spleen and brain, and can play an important role in various diseases. For example, when human allergic dermatitis (AD) occurs, $CCR_4$ expressed by CD4+T cells has an increased expression in peripheral blood mononuclear cells (PBMCs), and the level of TARC in serum also correspondingly increases. This shows that the chemotactic response of $CCR_4$ expressed in cells is induced by TARC, and, when human allergic dermatitis occurs, Th2 cells selectively migrate to the damaged skin. The drugs useful for the treatment of allergic dermatitis mainly include antihistamines, bronchodilators, but they can only improve the symptoms, while having no effect on the development of disease. In addition, corticosteroids also have a certain effect for allergic dermatitis, but there is a potential safety hazard. There are studies to show that the antagonism of MDC or TARC can reduce the accumulation of T cells in inflammatory sites, and $CCR_4$ antagonists may be very effective for the treatment of allergic dermatitis.

The expression of $CCR_4$ is increased when rheumatoid arthritis, systemic lupus erythematosus, multiple sclerosis, etc. occur. By $CCR_4$ it is also possible to make MDC and TARC activate platelet, which suggests that $CCR_4$ may play an important role in platelet activation and thrombotic diseases associated therewith. $CCR_4$ can also be indirectly coupled with HIV-1, and meanwhile it is also a co-receptor of HIV-2.

In addition, $CCR_4$ is also closely related to pulmonary diseases such as chronic obstructive pneumonia, chronic bronchitis and asthma. $CCR_4$ can be restrictively expressed in cells involved in asthmatic reaction, and is considered to be a good target for the treatment of asthma. At present, chemokine receptor antagonists useful for the treatment of asthma that have entered clinical phase I mainly include $CXCR_2$, $CXCR_4$, $CCR_1$ and $CCR_5$ receptor antagonists, but not $CCR_4$ receptor antagonist. Therefore, the development of $CCR_4$ receptor antagonists has a good prospect.

CONTENTS OF THE INVENTION

Summary of the Invention

The object of the present invention is to search and develop small molecular compounds as $CCR_4$ receptor antagonists, useful for the treatment of asthma, allergic dermatitis and $CCR_4$-related diseases, risk factors or conditions.

The present inventors have found that the compounds of formula I are effective for antagonizing $CCR_4$ receptor.

Accordingly, in the first aspect of the present invention, there is provided a compound of formula I,

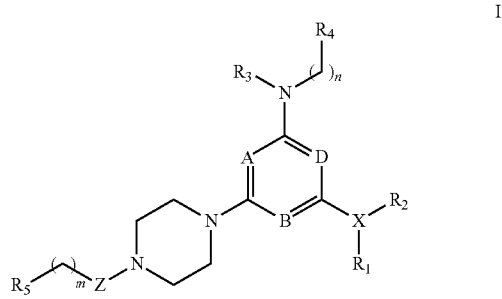

wherein:

any two of A, B and D are N and the other one is CH, preferably, A and B are N and D is CH;

Z is selected from the group consisting of —$CH_2$—, —C(O)— and —S(O)$_2$—;

X is halogen or N, with the proviso that when X is halogen, $R_1$ and $R_2$ in formula I are absent;

$R_1$ and $R_2$ are each independently selected from the group consisting of H, linear or branched alkyl having 1 to 6 carbon atoms, C1-C6 linear or branched heteroalkyl containing 1 to 2 heteroatoms independently selected from the group consisting of O, N and S; or $R_1$ and $R_2$, together with N to which they are attached, form a 5- to 8-membered heterocycloalkyl containing 1 to 2 heteroatoms independently selected from the group consisting of O, N and S; or $R_1$ is absent, D and $R_2$, together with N and other atoms to which they are attached, form a heteroaryl having 5 to 10 atoms;

$R_3$ and $R_4$ are each independently selected from the group consisting of H, aryl, heteroaryl, fused aryl or fused heteroaryl containing 5 to 10 atoms; wherein said aryl, heteroaryl, fused aryl or fused heteroaryl is optionally and independently mono-, di- or poly-substituted with a substituent selected from the group consisting of halogen, cyano, trifluoromethyl, hydroxy and nitro;

$R_5$ is selected from the group consisting of linear or branched alkyl having 1 to 6 carbon atoms, C1-C6 linear or branched heteroalkyl containing 1 to 2 heteroatoms independently selected from the group consisting of O, N and S, cycloalkyl group containing from 4 to 8, preferably from 5 to 8, more preferably from 5 or 6 carbon atoms, 5- to 8-membered, preferably 5- or 6-membered heterocycloalkyl containing 1 to 2 heteroatoms independently selected from the group consisting of O, N and S;

m and n are each independently 0, 1 or 2;

or a stereoisomer, or a pharmaceutically acceptable salt or solvate thereof.

In one embodiment of the first aspect of the present invention, there is provided a compound of formula I according to the present invention, or a stereoisomer, or a pharmaceutically acceptable salt or solvate thereof, wherein A and B are N and D is CH.

In one embodiment of the first aspect of the present invention, there is provided a compound of formula I according to the present invention, or a stereoisomer, or a pharmaceutically acceptable salt or solvate thereof, wherein Z is —C(O)—.

In one embodiment of the first aspect of the present invention, there is provided a compound of formula I according to the present invention, or a stereoisomer, or a pharmaceutically acceptable salt or solvate thereof, wherein X is N.

In one embodiment of the first aspect of the present invention, there is provided a compound of formula I according to the present invention, or a stereoisomer, or a pharmaceutically acceptable salt or solvate thereof, wherein $R_3$ is H.

In one embodiment of the first aspect of the present invention, there is provided a compound of formula I according to the present invention, or a stereoisomer, or a pharmaceutically acceptable salt or solvate thereof, wherein n is 1.

In one embodiment of the first aspect of the present invention, there is provided a compound of formula I according to the present invention, or a stereoisomer, or a pharmaceutically acceptable salt or solvate thereof, wherein $R_4$ is phenyl optionally and independently mono-, di- or poly-substituted with a substituent selected from the group consisting of halogen, cyano, trifluoromethyl, hydroxy and nitro.

In one embodiment of the first aspect of the present invention, there is provided a compound of formula I according to the present invention, or a stereoisomer, or a pharmaceutically acceptable salt or solvate thereof, wherein m is 0.

In one embodiment of the first aspect of the present invention, there is provided a compound of formula I according to the present invention, or a stereoisomer, or a pharmaceutically acceptable salt or solvate thereof, wherein $R_5$ is selected from the group consisting of linear or branched alkyl having 1 to 6 carbon atoms, C1-C6 linear or branched heteroalkyl containing 1 to 2 heteroatoms independently selected from the group consisting of O, N and S, cycloalkyl group containing 5 or 6 carbon atoms, 5- or 6-membered heterocycloalkyl containing 1 to 2 heteroatoms independently selected from the group consisting of O, N and S.

In one embodiment of the first aspect of the present invention, there is provided a compound of formula I according to the present invention, wherein the aryl is selected from the group consisting of phenyl, naphthyl, anthryl, phenanthryl, indenyl, fluorenyl and acenaphthylenyl, preferably selected from the group consisting of phenyl and naphthyl, more preferably selected from phenyl.

In one embodiment of the first aspect of the present invention, there is provided a compound of formula I according to the present invention, wherein the heteroaryl is selected from the group consisting of: pyridyl, pyrrolyl, furyl, thienyl, pyrazolyl, imidazolyl, thiazolyl, oxazolyl, isoxazolyl, indolyl, benzofuranyl, carbazolyl, pyridazinyl, pyrazinyl, quinolyl, isoquinolyl, purinyl, phenothiazinyl and phenoxazinyl, preferably selected from the group consisting of pyridyl, pyrrolyl and pyrazolyl, more preferably selected from the group consisting of pyridyl and pyrrolyl, and most preferably selected from pyridyl.

In one embodiment of the first aspect of the present invention, there is provided a compound of formula I according to the invention or a pharmaceutically acceptable salt or solvate thereof, wherein the compound is selected from the group consisting of:

1-{4-{4-[(2,4-dichlorobenzyl)amino]-6-[(2,2-dimethoxyethyl)methylamino]pyrimidin-2-yl}piperazin-1-yl}propanone;

1-{4-{4-[(2,4-dichlorobenzyl)amino]-6-[(2,2-dimethoxyethyl)methylamino]pyrimidin-2-yl}piperazin-1-yl}-2-methylpropanone;

1-{4-{4-[(2,4-dichlorobenzyl)amino]-6-[(2,2-dimethoxyethyl)methylamino]pyrimidin-2-yl}piperazin-1-yl}-3-methylthiopropanone;

1-{4-{4-[bis(2-methoxyethyl)amino]-6-(2,4-dichlorobenzylamino)-pyrimidin-2-yl}piperazin-1-yl}propanone;

1-{4-{4-[bis(2-methoxyethyl)amino]-6-(2,4-dichlorobenzylamino)-pyrimidin-2-yl}piperazin-1-yl}-2-methylpropanone;

1-{4-{4-[bis(2-methoxyethyl)amino]-6-(2,4-dichlorobenzylamino)-pyrimidin-2-yl}piperazin-1-yl}-3-methylthiopropanone;

{4-{4-[bis(2-methoxyethyl)amino]-6-(2,4-dichlorobenzylamino)-pyrimidin-2-yl}piperazin-1-yl}cyclohexylmethanone;

(R)-{4-{4-chloro-6-[(2,4-dichlorobenzyl)amino]pyrimidin-2-yl}piperazin-1-yl}(piperidin-2-yl)methanone;

(R)-{4-{4-chloro-6-[(2,4-dichlorobenzyl)amino]pyrimidin-2-yl}piperazin-1-yl}(thiomorpholin-3-yl)methanone;

1-{4-{4-[(2,4-dichlorobenzyl)amino]pyrido[2,3-d]pyrimidin-2-yl}piperazin-1-yl}propanone;

1-{4-{4-[(2,4-dichlorobenzyl)amino]pyrido[2,3-d]pyrimidin-2-yl}piperazin-1-yl}-2-methylpropanone;

cyclohexyl{4-{4-[(2,4-dichlorobenzyl)amino]pyrido[2,3-d]pyrimidin-2-yl}piperazin-1-yl}methanone;

4-[(2,4-dichlorobenzyl)amino]-2-(4-propylpiperazin-1-yl)pyrido[2,3-d]pyrimidine; and (R)-{4-{4-[(2,4-dichlorobenzyl)amino]pyrido[2,3-d]pyrimidin-2-yl}piperazin-1-yl}(thiomorpholin-3-yl)methanone.

In the second aspect of the present invention, there is provided use of a compound of formula I, a racemate or a stereoisomer or a pharmaceutically acceptable salt or solvate thereof, according to the first aspect of the present invention, for the treatment or prevention of $CCR_4$-related diseases or disorders.

In the third aspect of the present invention, there is provided a method of preparing a compound of formula I according to the first aspect of the present invention, the method comprising the steps of:

1) reacting 2,4,6-trichloropyrimidine with mono-protected piperazine in the presence of an acid-binding agent, to give a compound of formula 1,

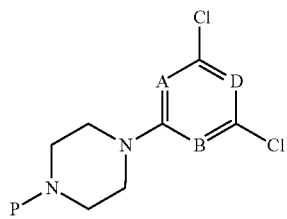

1 wherein A, B and D are as defined above in formula I, P is a nitrogen protective group;

2) reacting the compound of formula 1 with a $R_3$- and —$(CH_2)_n$—$R_4$-substituted amine in the presence of an acid-binding agent, to give a compound of formula 2,

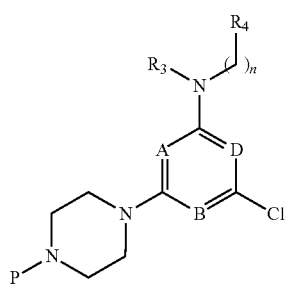

2 wherein A, B, D, $R_3$, $R_4$ and n are as defined above in formula I, P is a nitrogen protective group;

3) reacting the compound of formula 2 with a $R_1$- and $R_2$-substituted amine in the presence of an acid-binding agent, to give a compound of formula 3,

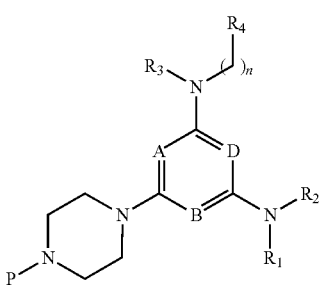

3 wherein A, B, D, $R_1$, $R_2$, $R_3$, $R_4$ and n are as defined above in formula I, P is a nitrogen protective group;

4) removing the protective group P from the compound of formula 3, and then reacting it with $R_5$-substituted carboxylic acid, acyl halide, sulfonyl chloride or halogenated hydrocarbon, to give a compound of formula 4,

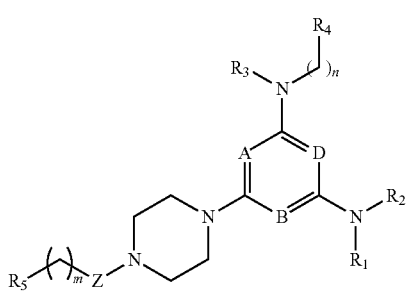

4 wherein A, B, D, $R_1$, $R_2$, $R_3$, $R_4$, $R_5$, n and m are as defined above in formula I;

or 5) when X is halogen, the compound of formula I is prepared according to the following reaction route: removing the protective group P from the compound of formula 2, and reacting it with $R_5$-substituted carboxylic acid, acyl halide, sulfonyl chloride or halogenated hydrocarbon, to give a compound of formula 5,

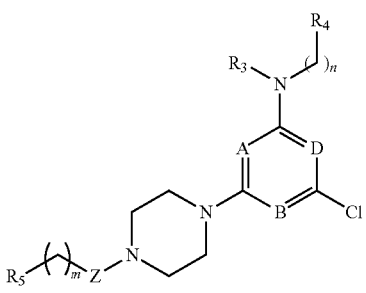

5 wherein A, B, D, Z, $R_3$, $R_4$, $R_5$, n and m are as defined above in formula I;

or 6) when $R_1$ is absent, D and $R_2$, together with N and other atoms to which they are attached, form a heteroaryl having 5 to 10 atoms, the compound of formula I is prepared according to the following reaction scheme:

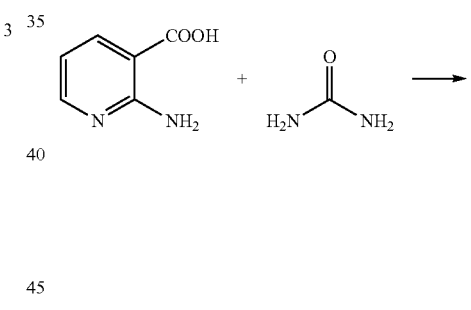

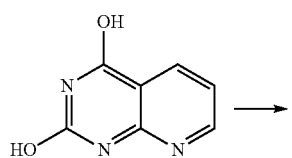

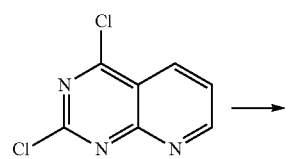

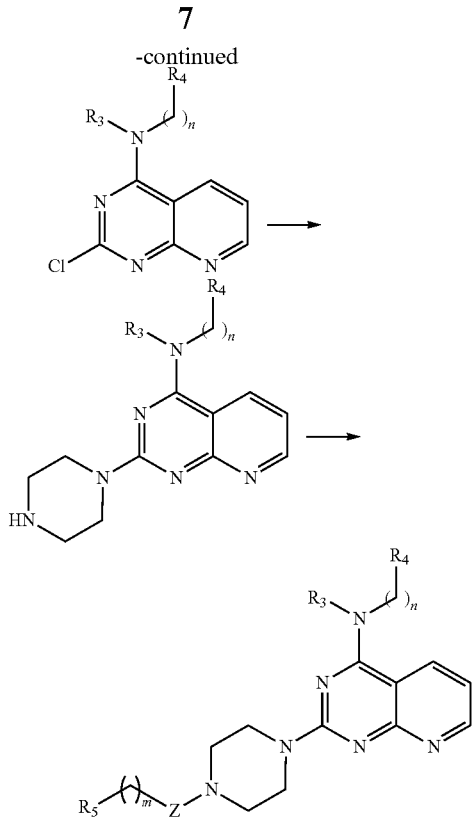

wherein Z, $R_3$, $R_4$, $R_5$ and n are as defined above in formula I.

In the fourth aspect of the present invention, there is provided a pharmaceutical composition comprising a compound of formula I, a racemate or a stereoisomer or a pharmaceutically acceptable salt or solvate thereof, according to the first aspect of the invention, and at least one pharmaceutically acceptable carrier, diluent or excipient.

In the fifth aspect of the present invention, there is provided use of a compound of formula I, a racemate or a stereoisomer or a pharmaceutically acceptable salt or solvate thereof, according to the first aspect of the invention, in the preparation of a medicament for the treatment or prevention of $CCR_4$-related diseases or disorders.

In the sixth aspect of the present invention, there is provided a method of treating or preventing $CCR_4$-related diseases or disorders, the method comprising administering a therapeutically or prophylactically effective amount of a compound of formula I, a racemate or a stereoisomer or a pharmaceutically acceptable salt or solvate thereof, according to the first aspect of the invention, to a subject in need thereof.

The $CCR_4$-related disease or disorder according to the present invention includes, but not limited to, autoimmune diseases, allergic inflammation, thrombotic diseases, atopic dermatitis, allergic rhinitis, asthma, allergic dermatitis, rheumatic arthritis, rheumatoid arthritis and lupus. Specifically, the $CCR_4$-related disease or disorder according to the present invention is allergic rhinitis, asthma, allergic dermatitis, rheumatic arthritis or rheumatoid arthritis.

DETAILED DESCRIPTION OF THE INVENTION

As used herein, the term "alkyl" refers to a saturated linear or branched monovalent hydrocarbon group having 1-20 carbon atoms (i.e., $C_{1-20}$ alkyl). In some embodiments, the alkyl has 1-10 carbon atoms (i.e., $C_{1-10}$ alkyl), preferably 1-6 carbon atoms (i.e., $C_{1-6}$ alkyl), 1 to 4 carbon atoms (i.e., $C_{1-4}$ alkyl) or 1-3 carbon atoms (i.e., $C_{1-3}$ alkyl). Examples of "alkyl" include, but not limited to, methyl, ethyl, n-propyl, isopropyl, n-butyl, t-butyl, n-pentyl, neopentyl, n-hexyl, 2-methylpentyl, 2,2-dimethylbutyl, 3,3-dimethylbutyl and the like.

As used herein, the term "cycloalkyl" refers to a cyclic hydrocarbon group having 3-12 carbon atoms, preferably 3-8 carbon atoms, more preferably 5-6 carbon atoms and having a single ring or multiple fused rings or a bridged ring system. As examples, such cycloalkyl may include: single ring structures such as cyclopropyl, cyclobutyl, cyclopentyl, cyclooctyl, 1-methyl-cyclopropyl, 2-methyl-cyclopentyl, 2-methyl cyclooctyl and the like; and polycyclic structures such as adamantyl and the like.

As used herein, the term "heterocycloalkyl" refers to cyloalkyl as defined above of which one or more carbon atoms are independently replaced with heteroatoms selected from the group consisting of N, O and S. Examples of heterocycloalkyl include, but not limited to, pyrrolidinyl, morpholinyl, piperazinyl, piperidinyl, and the like.

As used herein, the term "aryl" refers to an aromatic carbocyclic group having 5-18 carbon atoms and having a single ring or multiple fused rings. The aryl preferably has 5-10, 5-8 or 5-6 or 6 carbon atoms. Examples of the "aryl" include, but not limited to, phenyl, naphthyl, anthryl, phenanthryl, indenyl, fluorenyl and acenaphthylenyl, which may be optionally mono- or poly-substituted.

As used herein, the term "heteroaryl" refers to a heteroaromatic ring group having 5-18, preferably 5-14, more preferably 5-10 members, including monocyclic heteroaromatic rings and polycyclic heteroaromatic rings, wherein monocyclic aromatic ring is fused with one or more other aromatic rings. Heteroaryl has one or more ring heteroatoms independently selected from the group consisting of N, O and S. As used herein, the term "heteroaryl" also includes groups in which aromatic ring is fused with one or more non-aromatic rings (carbocyclic rings or heterocyclic rings), where the linking group or point is located on the aromatic ring. Examples of "heteroaryl" include, but not limited to, pyridyl, pyrrolyl, furyl, thienyl, pyrazolyl, imidazolyl, thiazolyl, oxazolyl, isoxazolyl, indolyl, benzofuranyl, benzimidazolyl, carbazolyl, pyridazinyl, pyrimidinyl, pyrazinyl, quinolyl, isoquinolyl, purinyl, phenothiazinyl, phenoxazolyl, and the like, which may be optionally mono- or poly-substituted.

As used herein, the term "fused aryl" has its general meaning as well known in the art, which forms a radical moiety in the compound of formula I, and generally includes, but not limited to, the examples of fused aryl listed herein.

As used herein, the term "fused heteroaryl" has its general meaning as well known in the art, which forms a radical moiety in the compound of formula I, and generally includes, but not limited to, the examples of fused heteroaryl listed herein.

As used herein, the term "halogen" refers to fluoro, chloro, bromo or iodo. Preferably, halo is fluoro or chloro, more preferably chloro. As used herein, the term "halogen" may also include its isotopic form.

As used herein, the groups represented by the following terms have their general meanings as well known in the art: nitrile, trifluoromethyl, trifluoromethoxy, hydroxyl, nitro, carboxyalkyl, alkoxycarbonyl, alkoxycarbonylalkyl, acyl, carboxamidoalkyl, alkyl, cycloalkyl, alkylthio, alkylsulfinyl, alkylsulfonyl, sulfamoyl, amidino, cyano, amino, amido, alkylamino, dialkylamino, alkylaminoalkyl.

As used herein, the phrase "C1-C6 linear or branched heteroalkyl containing 1 to 2 heteroatoms independently selected from the group consisting of O, N and S" has its general meaning as well known in the art, and moreover, it may herein particularly refer to the linear or branched alkyl, the carbon atom on which is replaced with O, N or S.

As used herein, the phrase "5- to 8-membered heterocycloalkyl containing 1 to 2 heteroatoms independently selected from the group consisting of O, N and S" has its general meaning as well known in the art, and moreover, it may herein particularly refer to the heterocycloalkyl, the carbon atom on which ring is replaced with O, N or S.

As used herein, the terms "racemate" and "enantiomers" have their general meanings as well known in the art.

As used herein, the terms "protective group" and "protecting group" can be used interchangeably and refer to a reagent which is used to temporarily block one or more desired functional groups on a compound having a plurality of reaction sites. In some embodiments, the protective group has one or more or preferably all of the following characteristics: a) it is selectively added in good yield to the functional group to give a protected substrate; b) the protected substrate is stable to the reaction(s) occurred at one or more other reaction sites; and c) it is selectively removed in good yield by a reagent that does not attack the regenerated deprotected functional group. As will be appreciated by a person skilled in the art, in some cases, the reagent does not attack other reactive groups on the compound. In other cases, the reagent may also react with other reactive groups on the compound. Examples of protective groups are described in details in Greene, T. W., Wuts, P. G., "Protective Groups in Organic Synthesis", 3$^{rd}$ Edition, John Wiley & Sons, New York: 1999 (and other editions of the book). The entire contents of these literatures are incorporated herein by reference. As used herein, the term "nitrogen protective group" refers to a reagent which is used to temporarily block one or more desired nitrogen reactive sites on a polyfunctional compound. Preferred nitrogen protective groups also has typical characteristics of the aforesaid protective groups and some typical nitrogen protective groups are also described in details in Greene, T. W., Wuts, P. G.'s "Protective Groups in Organic Synthesis", 3$^{rd}$ Edition, John Wiley & Sons, New York: 1999, Chapter 7. The entire contents of this literature are incorporated herein by reference.

As used herein, the term "pharmaceutically acceptable" generally refers to a form which is pharmaceutically or medically available, or if not being directly pharmaceutically or medically available, it can be available as an intermediate of pharmaceutical or medical product, and is then removed by a suitable method prior to the final application in pharmaceutical or medical. For example, a pharmaceutically acceptable salt includes not only pharmaceutically acceptable salts that can be used clinically, but also those which cannot be directly used clinically, but can be used in the preparation of the compound of the present invention and then removed in the subsequent procedure.

As used herein, the term "pharmaceutically acceptable carrier, diluent or excipient" means pharmaceutical adjuvants commonly used in the field of preparation industry, for example, those listed in, Luo Mingsheng et al, "Encyclopedia of Pharmaceutical Adjuvants", Science and Technology Press, Sichuan, 1995.

As used herein, the term "isomer" includes all possible isomers (e.g., enantiomers, diastereomers, geometrical isomers, conformational isomers, epimers and rotamers) of the compound of formula I of the present invention. For example, the respective R and S configurations of asymmetric centers, (Z) and (E) double bond isomers and (Z) and (E) conformational isomers are included in the present invention.

The compound of the present invention may exist in the form of non-solvate and solvate, including hydrated form, e.g., hemihydrate. Generally, to the object of the present invention, solvate form with pharmaceutically acceptable solvent such as water and ethanol is equivalent to non-solvate form.

According to the present invention, the compound of formula I and a pharmaceutically acceptable salt or a solvate thereof can be prepared using the following typical exemplary method, the method comprising the steps of:

1) At room temperature, a solution of mono-protected piperazine and an acid-binding agent such as N,N-diisopropylethylamine in dichloromethane is added dropwise to a solution of 2,4,6-trichloropyrimidine in dichloromethane, and stirred for two hours. Thereafter, organic salts are washed off with water and saturated brine respectively. The reaction product is subjected to separation and purification through a silica gel column chromatography with petroleum ether/ethyl acetate as eluent, to give a compound of formula 1,

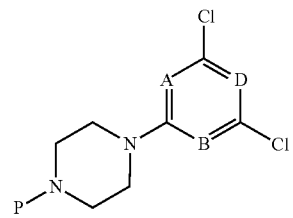

wherein A, B and D are as defined above in formula I, P is a nitrogen protective group;

2) The compound of formula 1, a R$_3$- and —(CH$_2$)$_n$—R$_4$-substituted amine and an acid-binding agent such as N,N-diisopropylethylamine are dissolved in NMP, heated to 90° C., and stirred overnight. Thereafter, the reaction product is diluted 5 folds with ethyl acetate, washed 6 times with water, washed 3 times with saturated brine, and then subjected to separation and purification through a silica gel column chromatography with petroleum ether/ethyl acetate as eluent, to give a compound of formula 2,

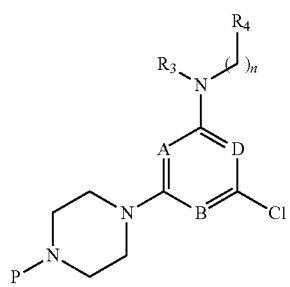

wherein A, B, D, R$_3$, R$_4$ and n are as defined above in formula I, P is a nitrogen protective group;

3) The compound of formula 2 is mixed with 15 folds of a $R_1$- and $R_2$-substituted amine, which amine acts as both a reactant and an acid-binding agent, and refluxed for 24 hours. Thereafter, the reaction product is diluted 5 folds with ethyl acetate, washed 6 times with water, washed 3 times with saturated brine, and then subjected to separation and purification through a silica gel column chromatography with petroleum ether/ethyl acetate as eluent, to give a compound of formula 3,

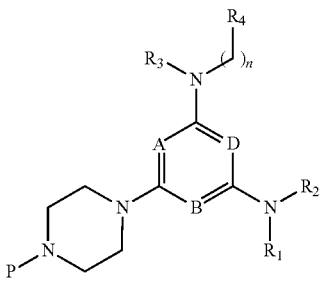

3 wherein A, B, D, $R_1$, $R_2$, $R_3$, $R_4$ and n are as defined above in formula I, P is a nitrogen protective group;

4) Equal volumes of ethanol and 10% aqueous sodium hydroxide solution are mixed, in which the compound of Formula 3 is dissolved, and then stirred at reflux for 24 hours. After removal of the protective group P, the resulting product is reacted with $R_5$-substituted carboxylic acid, acyl halide, sulfonyl chloride or halogenated hydrocarbon, to give a compound of formula 4,

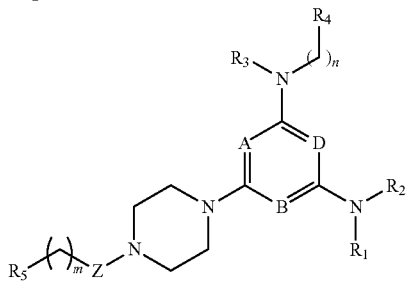

4 wherein A, B, D, Z, $R_1$, $R_2$, $R_3$, $R_4$, $R_5$, n and m are as defined above in formula I;

5) When X is halogen, the compound of formula I is prepared according to the following reaction route: equal volumes of ethanol and 10% aqueous sodium hydroxide solution are mixed, in which the compound of formula 2 is dissolved, and then stirred at reflux for 24 hours. After removal of the protective group P, the resulting product is reacted with $R_5$-substituted carboxylic acid, acyl halide, sulfonyl chloride or halogenated hydrocarbon, to give a compound of formula 5,

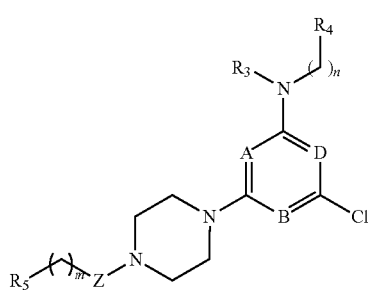

5 wherein A, B, D, Z, $R_3$, $R_4$, $R_5$, n and m are as defined above in formula I;

6) When $R_1$ is absent, D and $R_2$, together with N and other atoms to which they are attached, form a heteroaryl having 5 to 10 atoms, the compound of formula I is prepared according to the following reaction route: 2-aminonicotinic acid and urea are ground finely and mixed uniformly, heated to 210° C., kept at this temperature for 15 minutes, and then cooled to recrystallize; the resulting product is subjected to chlorination reaction by reflux in phosphorus oxychloride, to nucleophilic substitution reaction with a $R_3$- and —$(CH_2)_n$—$R_4$-substituted amine, and then to nucleophilic substitution reaction with piperazine, and is finally reacted with $R_5$-substituted carboxylic acid, acyl halide, sulfonyl chloride or halogenated hydrocarbon, to give the compound of formula I,

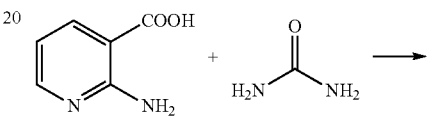

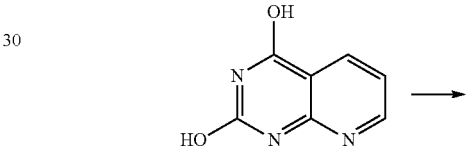

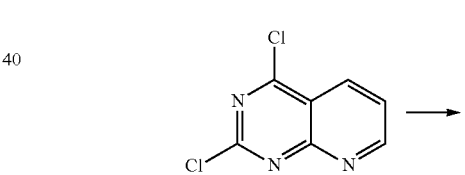

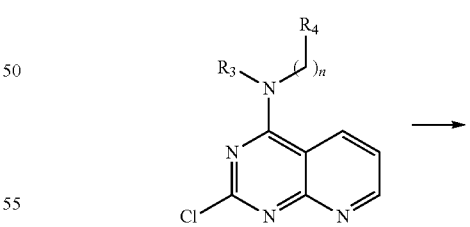

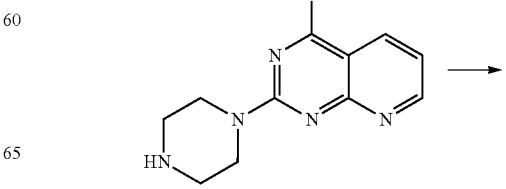

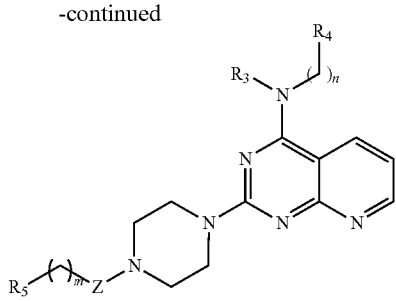

wherein Z, $R_3$, $R_4$, $R_5$, n and m are as defined above in formula I.

The person skilled in the art should recognize that the compound of formula I of the present invention may also be used in the form of a pharmaceutically acceptable salt or a solvate thereof. The pharmaceutically acceptable salt of the compound of formula I includes conventional salts formed by pharmaceutically acceptable inorganic acid or organic acid or inorganic base or organic base and acid addition salts of quaternary ammonium. More specific examples of suitable acid salts include salts of hydrochloric acid, hydrobromic acid, sulfuric acid, phosphoric acid, nitric acid, perchloric acid, fumaric acid, acetic acid, propionic acid, succinic acid, glycolic acid, formic acid, lactic acid, maleic acid, tartaric acid, citric acid, pamoic acid, malonic acid, hydroxymaleic acid, phenylacetic acid, glutamic acid, benzoic acid, salicylic acid, fumaric acid, toluenesulfonic acid, methanesulfonic acid, naphthalene-2-sulfonic acid, benzenesulfonic acid, hydroxynaphthoic acid, hydroiodic acid, malic acid, stearic acid, tannic acid and the like. As to other acids such as oxalic acid, while not being pharmaceutically acceptable in themselves, they can be used for the preparation of salt useful as intermediate, to thereby obtain the compound of the present invention and pharmaceutically acceptable salt thereof. More specific examples of suitable base salts include salts of sodium, lithium, potassium, magnesium, aluminum, calcium, zinc, N,N'-dibenzylethylenediamine, chloroprocaine, choline, diethanolamine, ethylenediamine, N-methylglucamine and procaine.

The present invention also includes a prodrug of the compound of formula I, which prodrug, once administered, can undergo chemical conversion through metabolic process to become an active drug. In general, such prodrug is a functional derivative of the compound of the present invention, which is readily converted in vivo into the required compound of formula I. For example, in "Design Of Prodrugs", H Bund Saard, Elsevier, 1985, conventional methods for the selection and preparation of suitable prodrug derivatives are described. The entire contents of this literature are incorporated herein by reference.

The present invention also includes an active metabolite of the compound of formula I.

Another aspect of the present invention relates to a pharmaceutical composition comprising a compound of formula I, a racemate or a stereoisomer or a pharmaceutically acceptable salt or solvate thereof and at least one pharmaceutically acceptable carrier, which can be used for in vivo treatment and has biocompatibility. The pharmaceutical composition may be prepared into various forms according to different administration routes. The compounds mentioned in the present invention may also be prepared into various pharmaceutically acceptable salts.

The pharmaceutical composition of the present invention comprises an effective dose of a compound of formula I, a racemate or a stereoisomer or a pharmaceutically acceptable salt or solvate thereof such as hydrate according to the present invention, and one or more suitable pharmaceutically acceptable carriers. The pharmaceutically acceptable carrier herein includes, but not limited to: ion exchanger, alumina, aluminum stearate, lecithin, serum protein such as human serum albumin, buffer agent such as phosphate, glycerin, sorbic acid, potassium sorbate, partial glyceride mixtures of saturated vegetable fatty acids, water, salt or electrolyte such as protamine sulfate, disodium hydrogen phosphate, potassium hydrogen phosphate, sodium chloride, zinc salt, colloidal silica, magnesium trisilicate, polyvinylpyrrolidone, cellulose-based substances, polyethylene glycol, sodium carboxymethylcellulose, polyacrylates, beeswax, lanolin.

The pharmaceutical composition comprising the compound of the present invention may be administered in any of the following modes: orally, inhalation by spraying, rectally, nasally, buccally, topically, parenterally, such as subcutaneous, intravenous, intramuscular, intraperitoneal, intrathecal, intraventricular, intrasternal and intracranial injection or infusion, or by the aid of an explant reservoir. Among them, the oral, intraperitoneal or intravenous administration mode is preferred.

When administered orally, the compound of the present invention can be made into any orally acceptable preparation form, including, but not limited to, tablets, capsules, aqueous solutions or suspensions. Wherein, the carrier used in tablets generally includes lactose and corn starch, and additionally, a lubricant such as magnesium stearate can also be added. Diluent used in capsules generally includes lactose and dried corn starch. Aqueous suspension is generally used by mixing active ingredient with a suitable emulsifier and suspending agent. If necessary, in the above oral preparations, certain sweetening agent, flavoring agent or coloring agent can also be added.

When administered topically, especially in the case of treating affected surface or organ where topical application easily reaches, such as ocular, dermal or lower intestinal nervous disorders, the compound of the present invention can be made into different topical preparation forms according to different affected surfaces or organs, as described below:

In the case of topical ocular administration, the compound of the present invention can be formulated into the preparation form of a micronised suspension or solution, wherein the carrier used is an isotonic sterile saline of a certain pH, in which a preservative, such as benzyl chloride alkoxide, may be added or not. For ocular administration, the compound can also be made into an ointment form such as vaseline ointment.

When topically administered to skin, the compound of the present invention can be made into suitable ointment, lotion or cream preparation form, wherein active ingredient is suspended or dissolved in one or more carriers. The carrier which can be used in ointment preparation includes, but not limited to: mineral oil, liquid petrolatum, white petrolatum, propylene glycol, polyoxyethylene, polyoxypropylene, emulsifying wax and water; the carrier which can be used in lotion or cream includes, but not limited to: mineral oil, sorbitan monostearate, Tween 60, cetyl alkyl esters wax, hexadecene aryl alcohol, 2-octyldodecanol, benzyl alcohol and water.

The compound of the present invention can also be administered in the form of sterile injectable preparation, including sterile injectable aqueous or oily suspension or sterile injectable solution. Wherein, the carrier and solvent used include water, Ringer's solution and isotonic sodium chloride solution. Further, sterile nonvolatile oil can also be used as the solvent or suspending medium, for example, mono- or di-glycerides.

Also to be noted is that the dose and use method of the compound of the present invention depend on many factors including the patient's age, weight, gender, natural health status, nutritional status, the active intensity of the compound, the time of taking, the metabolic rate, the severity of the disease and the physician's subjective judgment. The preferred dose is between 0.001 and 100 mg/kg body weight/day, more preferably between 0.01 and 50 mg/kg body weight/day, still more preferably between 0.1 and 25 mg/kg body weight/day, and most preferably between 1 and 10 mg/kg body weight/day. If desired, an effective daily dose can be divided into multiple doses for the purpose of administration. Therefore, a single dose composition can contain such dose or its divided dose, to make up the daily dose. The frequency that the compound of formula I is administered can be determined according to the clinician's experience and various factors including the patient's age, weight, sex, general health conditions, the type and severity of the disease and the like, for example, administered 1, 2, 3, 4, 5 or more times per day, or once every two days, once every three days, once every one week, once every two weeks and the like.

As to the patents, the patent applications, the publications and the like mentioned in the present invention, the entire contents thereof, as one part of the present invention, are incorporated herein by reference.

MODE OF CARRYING OUT THE PRESENT INVENTION

The present invention is further described by using specific intermediates and examples below. However, it is to be understood that these intermediates and examples are merely used to describe the present invention more detailedly and specifically, and should not be construed to restrict the present invention in any way.

The materials and test methods used in the tests are given general and/or specific description in the present invention. Although many materials and procedures used for achieving the object of the present invention are well known in the art, they are still described as detailedly as possible in the present invention. To be clear to a person skilled in the art, in the following text, if not otherwise specified, the materials and procedures used in the present invention are well known in the art.

Melting point of compound is measured by a YRT-3 type melting point apparatus, temperature being uncorrected. $^1$H-NMR spectrum is measured by a Bruker ARX 400 type NMR spectrometer. FAB mass spectrometry is measured by a Zabspect high resolution magnetic spectrometer.

PREPARATION OF INTERMEDIATES

Intermediate 1

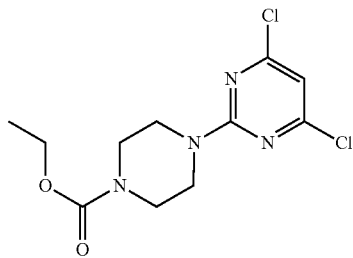

To a 1000 mL two-neck round bottom flask equipped with a thermometer and a constant pressure funnel, dichloromethane (350 mL) and 2,4,6-trichloropyrimidine (20 g, 0.109 mol) were added; to the constant pressure funnel, a solution of 1-ethoxycarbonyl piperazine (19 g, 0.120 mol) and N,N-diisopropylethylamine (15.5 g, 0.120 mol) in dichloromethane (150 mL) was charged, and slowly added dropwise while keeping the temperature below 30° C. After completion of the dropwise addition, the system was stirred for 2 hours. After completion of reaction, the reaction product was washed 3 times with 200 mL of water, washed 3 times with 200 mL of saturated brine, concentrated, and separated through a silica gel column (eluent: petroleum ether/ethyl acetate), to give 8.0 g of a white solid product, yield 24.05%.

$^1$H-NMR (400 MHz, CDCl$_3$) δ ppm: 6.42 (1H, s), 4.18 (2H, m), 3.65-3.52 (8H, brm), 1.29 (3H, t, J=7.0 Hz, J=7.28 Hz); EI-MS (m/z): 305.1 [M+H]$^+$.

Intermediate 2

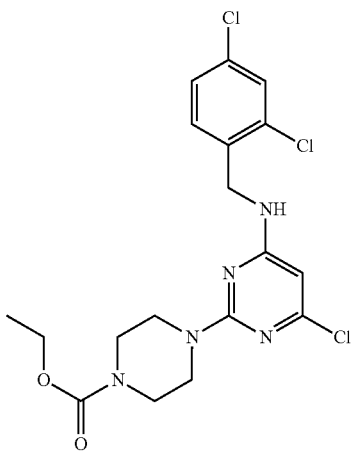

To a 250 mL two-neck round bottom flask equipped with a thermometer and a reflux condenser, Intermediate 1 (8.0 g, 0.026 mol), 2,4-dichlorobenzylamine (4.75 g, 0.027 mol), N,N-diisopropylethylamine (6.72 g, 0.052 mol) and NMP (80 mL) were added, mixed uniformly, heated to 90° C., and stirred for 12 hours. Thereafter, the reaction product was 5-fold diluted with ethyl acetate, washed 6 times with water, washed 3 times with saturated brine, concentrated, and separated through a silica gel column (eluent: petroleum ether/ethyl acetate), to give 10.8 g of a white solid product, yield 92.6%.

$^1$H-NMR (400 MHz, CDCl$_3$) δ ppm: 7.39 (1H, d, J=1.68 Hz), 7.34 (1H, d, J=8.4 Hz), 7.21 (1H, d, J=8.6 Hz), 4.94 (1H, s), 4.55 (2H, d, J=6.16 Hz), 4.18 (2H, m), 3.71-3.55 (8H, brm), 1.30 (3H, t, J=7.0 Hz, J=7.28 Hz); EI-MS (m/z): 444.2 [M+H]$^+$.

Intermediate 3

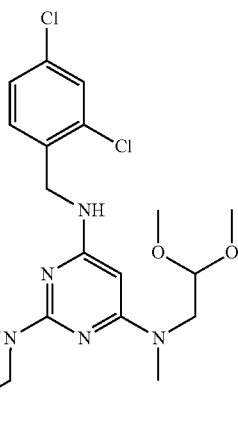

To a 100 mL two-neck round bottom flask equipped with a thermometer and a reflux condenser, Intermediate 2 (5.0 g, 0.011 mol) and 2-methylaminoacetaldehyde dimethyl acetal (19.64 g, 0.165 mol) were added, mixed uniformly, heated to reflux at 140° C., and stirred for 24 hours. Thereafter, the reaction product was 5-fold diluted with ethyl acetate, washed 3 times with water, washed 3 times with saturated brine, concentrated, and separated through a silica gel column (eluent: petroleum ether/ethyl acetate), to give 4.22 g of a white solid product, yield 71.2%.

$^1$H-NMR (400 MHz, CDCl$_3$) δ ppm: 7.38 (2H, m), 7.19 (1H, d, J=8.4 Hz), 4.85 (1H, m), 4.82 (1H, s), 4.53 (2H, d, J=6.16 Hz), 4.49 (1H, m), 4.13 (2H, m), 3.72 (4H, m), 3.58 (2H, d, J=5.2 Hz), 3.37 (6H, s), 2.95 (3H, s), 2.9 (4H, m), 1.32 (3H, t, J=7.0 Hz, J=7.28 Hz); EI-MS (m/z): 527.2 [M+H]$^+$.

Intermediate 4

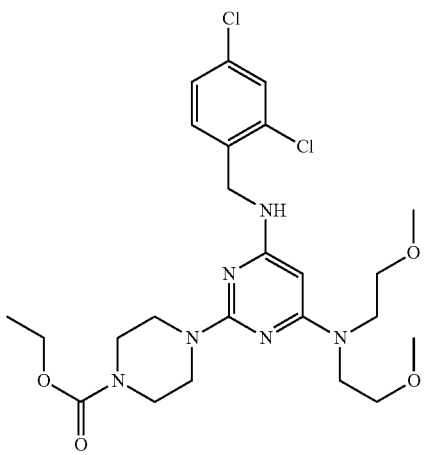

To a 100 mL two-neck round bottom flask equipped with a thermometer and a reflux condenser, Intermediate 2 (5.0 g, 0.011 mol) and dimethoxyethylamine (21.98 g, 0.165 mol) were added, mixed uniformly, heated to reflux at 168° C., and stirred for 24 hours. Thereafter, the reaction product was 5-fold diluted with ethyl acetate, washed 3 times with water, washed 3 times with saturated brine, concentrated, and separated through a silica gel column (eluent: petroleum ether/ethyl acetate), to give 3.63 g of a white solid product, yield 74.6%.

$^1$H-NMR (400 MHz, CDCl$_3$) δ ppm: 7.37 (2H, m), 7.18 (1H, d, J=8.4 Hz), 4.84 (2H, m), 4.51 (2H, d, J=6.4 Hz), 4.12 (2H, m), 3.68-3.47 (12H, brm), 3.3 (6H, s), 2.88 (4H, m), 1.31 (3H, t, J=7.0 Hz, J=7.28 Hz); EI-MS (m/z): 541.2 [M+H]$^+$.

Intermediate 5

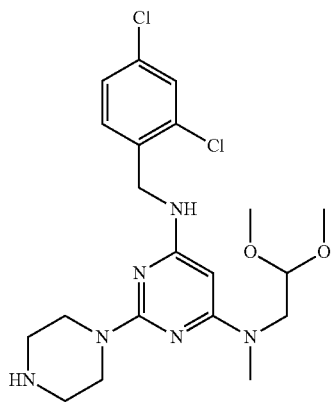

To a 500 mL two-neck round bottom flask equipped with a thermometer and a reflux condenser, Intermediate 3 (4.22 g, 0.009 mol), ethanol (90 mL) and a 10% sodium hydroxide aqueous solution (90 mL) were added, mixed uniformly, heated to reflux at 90° C., and stirred for 24 hours. Thereafter, the reaction product was subjected to vacuum distillation for removal of ethanol, and extracted 3 times with ethyl acetate. The extracts were combined, washed 3 times with saturated brine, concentrated, and separated through a silica gel column (eluent: petroleum ether/ethyl acetate/methanol), to give 3.61 g of an oily product, yield 88.1%.

$^1$H-NMR (400 MHz, CDCl$_3$) δ ppm: 7.38 (2H, m), 7.19 (1H, d, J=8.4 Hz), 4.85 (1H, m), 4.82 (1H, s), 4.53 (2H, d, J=6.16 Hz), 4.49 (1H, m), 3.72 (4H, m), 3.58 (2H, d, J=5.2 Hz), 3.37 (6H, s), 2.95 (3H, s), 2.9 (4H, m); EI-MS (m/z): 455.2 [M+H]$^+$.

Intermediate 6

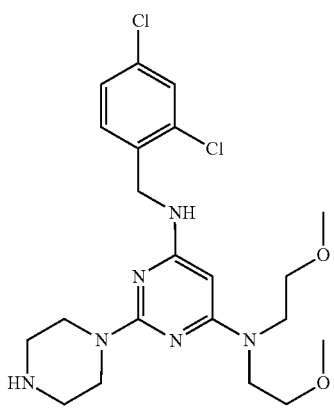

To a 500 mL two-neck round bottom flask equipped with a thermometer and a reflux condenser, Intermediate 4 (5.41 g, 0.010 mol), ethanol (100 mL) and a 10% sodium hydroxide aqueous solution (100 mL) were added, mixed uniformly, heated to reflux at 90° C., and stirred for 24 hours. Thereafter, the reaction product was subjected to vacuum distillation for removal of ethanol, and extracted 3 times with ethyl acetate. The extracts were combined, washed 3 times with saturated brine, concentrated, and separated through a silica gel column (eluent: petroleum ether/ethyl acetate/methanol), to give 4.46 g of an oily product, yield 95.0%.

$^1$H-NMR (400 MHz, CDCl$_3$) δ ppm: 7.37 (2H, m), 7.18 (1H, d, J=8.4 Hz), 4.84 (2H, m), 4.51 (2H, d, J=6.4 Hz), 3.68-3.47 (12H, brm), 3.3 (6H, s), 2.88 (4H, m); EI-MS (m/z): 469.4 [M+H]$^+$.

Intermediate 7

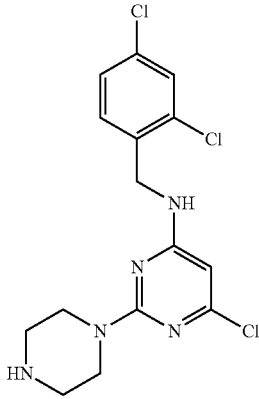

To a 500 mL two-neck round bottom flask equipped with a thermometer and a reflux condenser, Intermediate 2 (4.45 g, 0.010 mol), ethanol (100 mL) and a 10% sodium hydroxide aqueous solution (100 mL) were added, mixed uniformly, heated to reflux at 90° C., and stirred for 24 hours. Thereafter, the reaction product was subjected to vacuum distillation for removal of ethanol, and extracted 3 times with ethyl acetate. The extracts were combined, washed 3 times with saturated brine, concentrated, and separated through a silica gel column (eluent: petroleum ether/ethyl acetate/methanol), to give 3.54 g of a white foamy solid product, yield 95.0%.

$^1$H-NMR (400 MHz, CDCl$_3$) δ ppm: 7.42 (1H, d, J=1.12 Hz), 7.27 (2H, m), 5.75 (1H, s), 5.19 (1H, s), 4.58 (2H, s), 3.73 (4H, m), 3.01 (4H, m); EI-MS (m/z): 372.1 [M+H]$^+$.

Intermediate 8

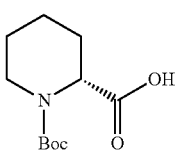

To a 1000 mL round bottom flask, 2R-piperidine carboxylic acid (8.0 g, 0.062 mol), di-tert-butyl dicarbonate (14.8 g, 0.068 mol), sodium bicarbonate (26.04 g, 0.310 mol) and methanol (400 mL) were added, and stirred at room temperature for 24 hours. Thereafter, the reaction product was subjected to vacuum distillation for removal of methanol, dissolved with water, washed 3 times with ethyl ether, adjusted to pH=2 with saturated potassium hydrogen sulfate, and extracted 3 times with dichloromethane. The extracts were combined, washed 3 times with saturated brine, concentrated, and separated through a silica gel column (eluent: petroleum ether/ethyl acetate/acetic acid), to give 12.48 g of a white product, yield 87.8%.

$^1$H-NMR (400 MHz, DMSO) δ ppm: 12.71 (1H, s), 4.61 (1H, d, J=28.8 Hz), 3.82 (1H, d, J=12 Hz), 2.93 (1H, m), 2.06 (1H, s), 1.62 (3H, m), 1.39 (11H, m); EI-MS (m/z): 229.1[M]$^+$.

Intermediate 9

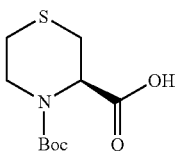

To a 1000 mL round bottom flask, 2R-thiomorpholine carboxylic acid, hydrochloride (10.0 g, 0.054 mol), di-tert-butyl dicarbonate (13.0 g, 0.060 mol), sodium bicarbonate (45.0 g, 0.536 mol) and methanol (500 mL) were added, and stirred at room temperature for 24 hours. Thereafter, the reaction product was subjected to vacuum distillation for removal of methanol, dissolved with water, washed 3 times with ethyl ether, adjusted to pH=2 with saturated potassium hydrogen sulfate, and extracted 3 times with dichloromethane. The extracts were combined, washed 3 times with saturated brine, concentrated, and separated through a silica gel column (eluent: petroleum ether/ethyl acetate/acetic acid), to give 8.63 g of a white product, yield 64.6%.

$^1$H-NMR (400 MHz, CDCl$_3$) δ ppm: 5.33 (1H, d, J=90.4 Hz), 4.39 (1H, brm), 3.30 (2H, brm), 2.95 (1H, m), 2.71 (1H, m), 2.53 (1H, m), 1.53 (9H, s); EI-MS (m/z): 247.1[M]$^+$.

Intermediate 10

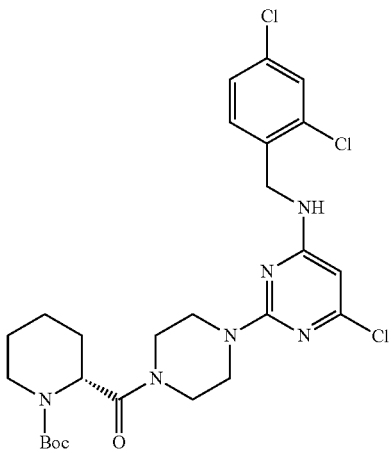

To a 25 mL round bottom flask, Intermediate 7 (540 mg, 1.45 mmol), the intermediate 8 (332 mg, 1.45 mmol), EDCI (418 mg, 2.18 mmol), HOBt (294 mg, 2.18 mmol), DIEA (374 mg, 2.9 mmol) and tetrahydrofuran (9 mL) were added, and stirred at room temperature overnight. Thereafter, the reaction product was subjected to vacuum distillation for removal of solvent, dissolved with water, and extracted 3 times with ethyl acetate. The extracts were combined, washed 3 times with saturated brine, concentrated, and separated through a silica gel column (eluent: petroleum ether/ethyl acetate), to give 650 mg of a white foamy solid product, yield 76.8%.

$^1$H-NMR (400 MHz, DMSO) δ ppm: 9.13 (1H, s), 8.63 (1H, s), 8.08 (1H, s), 7.64 (1H, d, J=1.52 Hz), 7.27 (2H, m), 5.97 (1H, s), 4.56 (2H, d, J=4.48 Hz), 4.39 (1H, d, J=9.24 Hz), 3.76-3.22 (9H, brm), 2.87 (1H, s), 1.99 (1H, m), 1.74 (4H, m), 1.45 (10H, m); EI-MS (m/z): 583.2 [M+H]$^+$.

Intermediate 11

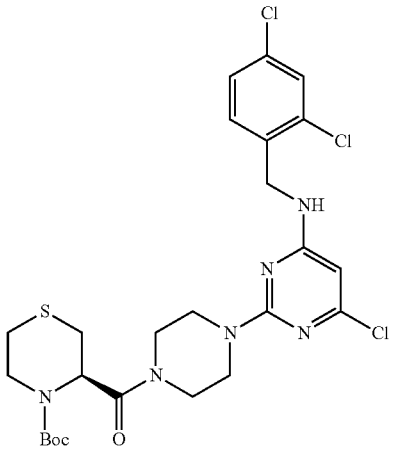

To a 25 mL round bottom flask, Intermediate 7 (540 mg, 1.45 mmol), Intermediate 9 (359 mg, 1.45 mmol), EDCI (418 mg, 2.18 mmol), HOBt (294 mg, 2.18 mmol), DIEA (374 mg, 2.9 mmol) and tetrahydrofuran (9 mL) were added, and stirred at room temperature overnight. Thereafter, the reaction product was subjected to vacuum distillation for removal of solvent, dissolved with water, and extracted 3 times with ethyl acetate. The extracts were combined, washed 3 times with saturated brine, concentrated, and separated through a silica gel column (eluent: petroleum ether/ethyl acetate), to give 688 mg of a white foamy solid product, yield 78.8%.

$^1$H-NMR (400 MHz, CDCl$_3$) δ ppm: 7.42 (1H, d, J=1.12 Hz), 7.27 (2H, m), 5.75 (1H, s), 5.19 (1H, s), 4.58 (2H, s), 3.95-3.44 (10H, brm), 3.12 (1H, m), 2.82 (2H, m), 2.43 (2H, m), 1.92 (9H, s); EI-MS (m/z): 601.1 [M+H]$^+$.

Intermediate 12

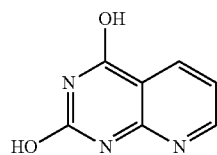

2-Aminonicotinic acid (5 g, 0.036 mol) and urea (9 g, 0.150 mol) were put into a mortar, ground finely and mixed uniformly. The resulting mixture was poured into a porcelain evaporating dish, heated in a heating mantle while continued stirring, and melted when the temperature rose up to 185° C. It was further heated to 210° C., and kept at this temperature for 15 minutes. Then, turn off the power. The reaction product was cooled, dissolved in 100 mL of 2 mol/L NaOH aqueous solution, and then heated to 80° C. till complete dissolution, followed by adding dropwise acetic acid until neutral, to give 3.2 g of a white crystal product, yield 54.2%.

$^1$H-NMR (400 MHz, DMSO) δ ppm: 11.69 (1H, s), 11.48 (1H, s), 8.61 (1H, m), 8.27 (1H, m), 7.26 (1H, m).

Intermediate 13

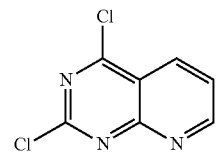

To a 500 mL two-neck round bottom flask equipped with a thermometer and a reflux condenser, Intermediate 12 (10.0 g, 0.061 mol) and phosphorous oxychloride (200 mL) were added, mixed uniformly, heated to reflux at 105° C. and stirred for 24 hours. Thereafter, the reaction product was subjected to vacuum distillation for removal of phosphorus oxychloride. The remaining syrupy substance was poured onto 200 g of crushed ice, and immediately extracted 3 times with chloroform, 150 mL each time. The extracts were combined, washed 3 times with saturated brine, concentrated, and separated through a silica gel column (eluent: petroleum ether/ethyl acetate), to give 10.36 g of a white solid product, yield 84.9%.

$^1$H-NMR (400 MHz, CDCl$_3$) δ ppm: 9.34 (1H, m), 8.66 (1H, m), 7.76 (1H, m); EI-MS (m/z): 199.0[M]$^+$.

Intermediate 14

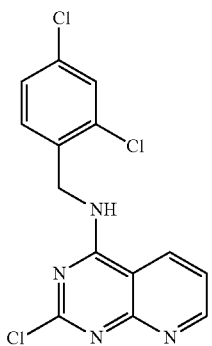

To a 250 mL two-neck round bottom flask equipped with a thermometer and a constant pressure funnel, Intermediate 13 (10.36 g, 0.052 mol), N,N-diisopropylethylamine (7.35 g, 0.057 mol) and 1,2-dichloroethane (80 mL) were added; to the constant pressure funnel, a solution of 2,4-dichlorobenzylamine (10.03 g, 0.057 mol) in 1,2-dichloroethane (10 mL) was charged, and slowly added dropwise at −10° C. After completion of the dropwise addition, the system was stirred overnight. Precipitated solid was filtered, and the filter cake was purified through a silica gel column (eluent: petroleum ether/ethyl acetate), to give 16.35 g of a white solid product, yield 92.6%.

$^1$H-NMR (400 MHz, DMSO) δ ppm: 9.57 (1H, m), 9.03 (1H, m), 8.79 (1H, m), 7.69 (1H, m), 7.64 (1H, m), 7.45 (2H, m), 4.79 (2H, d, J=5.2 Hz); EI-MS (m/z): 339.2 [M+H]$^+$.

Intermediate 15

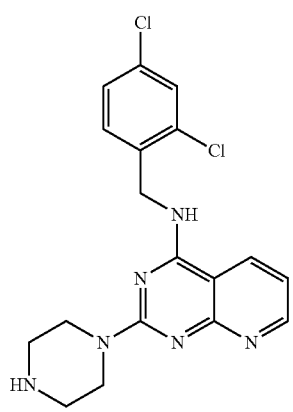

To a 2000 mL two-neck round bottom flask equipped with a thermometer and a reflux condenser, Intermediate 14 (16.35 g, 0.048 mol), piperazine (8.27 g, 0.096 mol) and ethanol (1200 mL) were added, heated to 60° C. and stirred for 15 hours. After concentration, the reaction product was dissolved with 300 mL of dichloromethane, washed 3 times with saturated brine, and purified through a silica gel column (eluent: ethyl acetate/methanol/ammonia) to give 13.86 g of a white solid product, yield 74.2%.

$^1$H-NMR (400 MHz, DMSO) δ ppm: 8.85 (1H, m), 8.66 (1H, m), 8.46 (1H, m), 7.63 (1H, m), 7.38 (2H, m), 7.10 (1H, m), 4.73 (2H, d, J=5.2 Hz), 3.63 (4H, s), 2.61 (4H, s); EI-MS (m/z): 389.2 [M+H]$^+$.

Intermediate 16

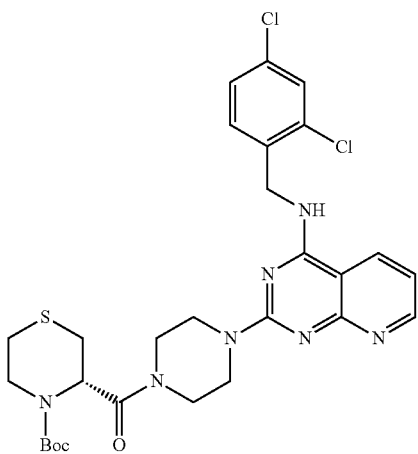

To a 100 mL round bottom flask, Intermediate 15 (1.28 g, 3.28 mmol), Intermediate 9 (0.81 g, 3.28 mmol), EDCI (0.94 g, 4.92 mmol), HOBt (0.66 g, 4.92 mmol), DIEA (0.85 g, 6.56 mmol) and tetrahydrofuran (40 mL) were added, and stirred at room temperature overnight. Thereafter, the reaction product was subjected to vacuum distillation for removal of solvent, dissolved with water, and extracted 3 times with ethyl acetate. The extracts were combined, washed 3 times with saturated brine, concentrated, and separated through a silica gel column (eluent: ethyl acetate/methanol/ammonia), to give 1.63 g of a white foamy solid product, yield 80.5%.

$^1$H-NMR (400 MHz, CDCl$_3$) δ ppm: 8.77 (1H, m), 8.02 (1H, m), 7.43 (1H, m), 7.31 (1H, m), 7.20 (1H, m), 7.05 (1H, m), 6.56 (1H, m), 4.85 (2H, d, J=5.2 Hz), 4.02-3.44 (10H, brm), 3.13 (1H, m), 2.83 (2H, m), 2.44 (2H, m), 2.02 (9H, s); EI-MS (m/z): 618.2 [M+H]$^+$.

EXAMPLE

Example 1

1-{4-{4-[(2,4-dichlorobenzyl)amino]-6-[(2,2-dimethoxyethyl)methylamino]pyrimidin-2-yl}piperazin-1-yl}propanone (Compound 1)

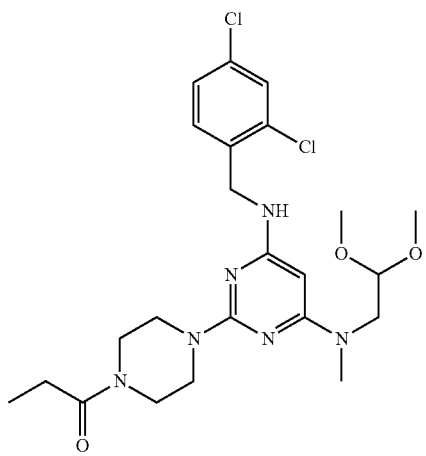 [SMILES: CCC(=O)N1CCN(c2nc(NCc3ccc(Cl)cc3Cl)cc(N(C)CC(OC)OC)n2)CC1]

Intermediate 5 (300 mg, 0.66 mmol), propionic acid (54 mg, 0.73 mmol), EDCI (190 mg, 0.99 mmol), HOBt (134 mg, 0.99 mmol), DIEA (170 mg, 1.32 mmol) were dissolved in tetrahydrofuran (9 mL), and stirred at room temperature overnight. Thereafter, the reaction product was subjected to vacuum distillation for removal of solvent, dissolved with water, and extracted 3 times with ethyl acetate. The extracts were combined, washed 3 times with saturated brine, concentrated, separated through a silica gel column (eluent: petroleum ether/ethyl acetate/ammonia), and recrystallized with ethyl acetate, n-hexane to give a white solid product.

$^1$H-NMR (400 MHz, CDCl$_3$) δ ppm: 7.39 (1H, d, J=1.96 Hz), 7.35 (1H, d, J=7.84 Hz), 7.20 (1H, d, J=8.4 Hz), 4.85 (1H, s), 4.53 (2H, d, J=6.2 Hz), 4.50 (1H, t, J=5.04 Hz, J=4.76 Hz), 3.71-3.47 (10H, brm), 3.37 (6H, s), 2.96 (3H, s), 2.41 (1H, m), 1.19 (3H, m); EI-MS (m/z): 511.3 [M+H]$^+$.

Example 2

1-{4-{4-[(2,4-dichlorobenzyl)amino]-6-[(2,2-dimethoxyethyl)methylamino]pyrimidin-2-yl}piperazin-1-yl}-2-methylpropanone (Compound 2)

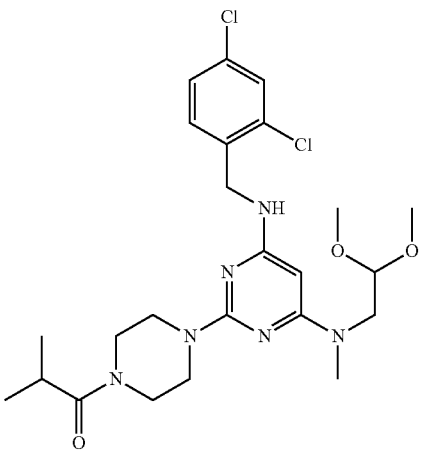 [SMILES: COC(CN(C)c1cc(NCc2ccc(Cl)cc2Cl)nc(N2CCN(C(=O)C(C)C)CC2)n1)OC]

Intermediate 5 and isobutyric acid were used as raw materials to go through the steps according to Example 1, to give a white solid product.

$^1$H-NMR (400 MHz, CDCl$_3$) δ ppm: 7.38 (1H, d, J=2.00 Hz), 7.35 (1H, d, J=8.12 Hz), 7.20 (1H, dd, J=2.24 Hz, J=2.36 Hz), 4.85 (1H, s), 4.53 (2H, d, J=6.44 Hz), 4.50 (1H, t, J=5.36 Hz, J=5.32 Hz), 3.75-3.50 (10H, brm), 3.37 (6H, s), 2.96 (3H, s), 2.84 (1H, m), 1.16 (6H, d, J=6.72 Hz); ELMS (m/z): 525.3 [M+H]$^+$.

Example 3

1-{4-{4-[(2,4-dichlorobenzyl)amino]-6-[(2,2-dimethoxyethyl)methylamino]pyrimidin-2-yl}piperazin-1-yl}-3-methylthiopropanone (Compound 3)

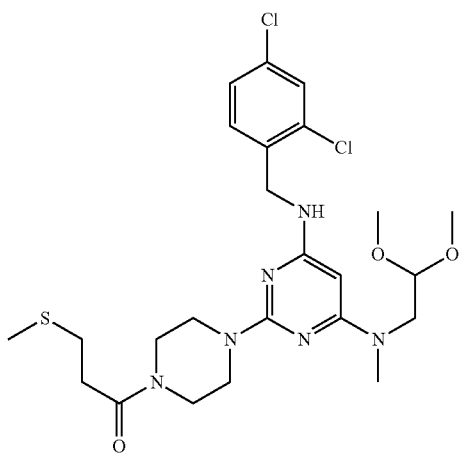

Intermediate 5 and 3-methylthiopropionic acid were used as raw materials to go through the steps according to Example 1, to give a white solid product.

$^1$H-NMR (400 MHz, CDCl$_3$) δ ppm: 7.39 (1H, d, J=1.96 Hz), 7.35 (1H, d, J=8.12 Hz), 7.20 (1H, dd, J=1.96 Hz, J=2.24 Hz), 4.85 (1H, s), 4.53 (2H, d, J=6.16 Hz), 4.48 (1H, t), 3.76-3.46 (10H, brm), 3.37 (6H, s), 2.96 (3H, s), 2.86 (2H, t, J=7.00 Hz, J=7.84 Hz), 2.68 (2H, t, J=8.12 Hz, J=7.04 Hz), 2.16 (3H, s); EI-MS (m/z): 557.2 [M+H]$^+$.

Example 4

1-{4-{4-[bis(2-methoxyethyl)amino]-6-(2,4-dichlorobenzylamino)-pyrimidin-2-yl}piperazin-1-yl}propanone (Compound 4)

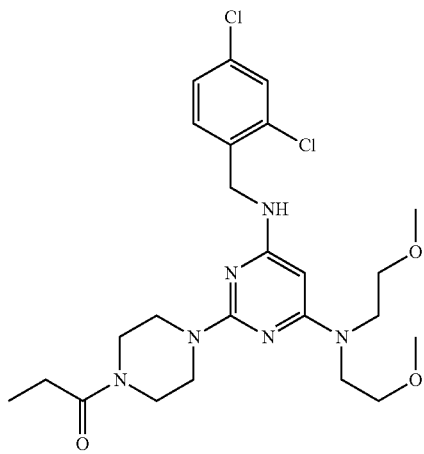 [SMILES: CCC(=O)N1CCN(c2nc(NCc3ccc(Cl)cc3Cl)cc(N(CCOC)CCOC)n2)CC1]

Intermediate 6 and propionic acid were used as raw materials to go through the steps according to Example 1, to give a white solid product.

$^1$H-NMR (400 MHz, CDCl$_3$) δ ppm: 7.38 (1H, d, J=1.96 Hz), 7.34 (1H, d, J=8.4 Hz), 7.20 (1H, dd, J=1.96 Hz, J=2.24 Hz), 4.88 (1H, s), 4.52 (2H, d, J=6.44 Hz), 3.73-3.59 (10H, brm), 3.49-3.44 (6H, brm), 3.30 (6H, s), 2.39 (2H, q, J=7.56 Hz, J=7.32 Hz, J=7.56 Hz), 1.19 (3H, t, J=7.32 Hz, J=7.56 Hz);
EI-MS (m/z): 525.0 [M+H]$^+$.

Example 5

1-{4-{4-[bis(2-methoxyethyl)amino]-6-(2,4-dichlorobenzylamino)-pyrimidin-2-yl}piperazin-1-yl}-2-methylpropanone (Compound 5)

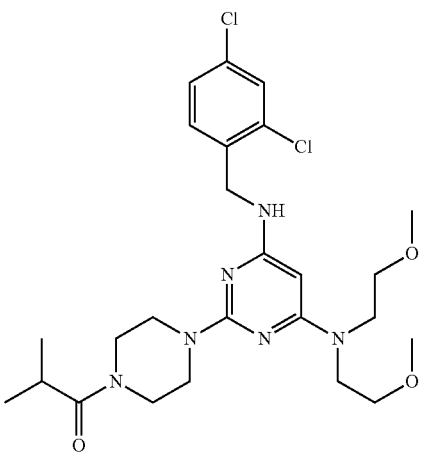 [SMILES: COCCN(CCOC)c1cc(NCc2ccc(Cl)cc2Cl)nc(N2CCN(C(=O)C(C)C)CC2)n1]

Intermediate 6 and isobutyric acid were used as raw materials to go through the steps according to Example 1, to give a white solid product.

$^1$H-NMR (400 MHz, CDCl$_3$) δ ppm: 7.38 (1H, d, J=1.96 Hz), 7.34 (1H, d, J=8.4 Hz), 7.20 (1H, dd, J=1.96 Hz, J=2.24 Hz), 4.88 (1H, s), 4.52 (2H, d, J=6.2 Hz), 3.72-3.46 (16H, brm), 3.30 (6H, s), 2.84 (1H, m), 1.16 (6H, d, J=6.76 Hz);
EI-MS (m/z): 539.1 [M+H]$^+$.

Example 6

1-{4-{4-[bis(2-methoxyethyl)amino]-6-(2,4-dichlorobenzylamino)-pyrimidin-2-yl}piperazin-1-yl}-3-methylthiopropanone (Compound 6)

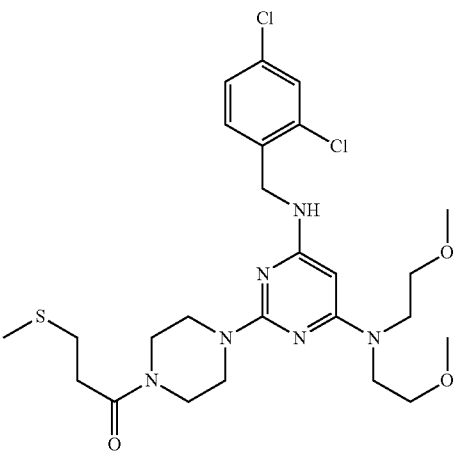

Intermediate 6 and 3-methylthiopropionic acid were used as raw materials to go through the steps according to Example 1, to give a white solid product.

¹H-NMR (400 MHz, CDCl₃) δ ppm: 7.38 (1H, d, J=1.96 Hz), 7.34 (1H, d, J=8.4 Hz), 7.20 (1H, dd, J=1.68 Hz, J=1.96 Hz), 4.88 (1H, s), 4.51 (2H, d, J=6.2 Hz), 3.74-3.47 (16H, brm), 3.30 (6H, s), 2.86 (2H, t, J=7.28 Hz, J=7.84 Hz), 2.67 (2H, t, J=7.84 Hz, J=6.96 Hz), 2.15 (3H, s); EI-MS (m/z): 571.2 [M+H]⁺.

Example 7

{4-{4-[bis(2-methoxyethyl)amino]-6-(2,4-dichlorobenzylamino)-pyrimidin-2-yl}piperazin-1-yl}cyclohexylmethanone (Compound 7)

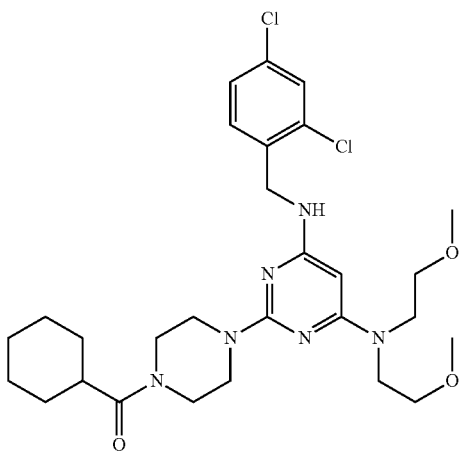 [SMILES: COCCN(CCOC)c1cc(NCc2ccc(Cl)cc2Cl)nc(N2CCN(C(=O)C3CCCCC3)CC2)n1]

Intermediate 6 and cyclohexyl carboxylic acid were used as raw materials to go through the steps according to Example 1, to give a white solid product.

¹H-NMR (400 MHz, CDCl₃) δ ppm: 7.38 (1H, d, J=1.96 Hz), 7.34 (1H, d, J=8.12 Hz), 7.20 (1H, dd, J=1.96 Hz, J=1.96 Hz), 4.88 (1H, s), 4.83 (1H, s), 4.52 (2H, d, J=6.16 Hz), 3.75-3.46 (16H, brm), 3.30 (6H, s), 2.50 (1H, m), 1, 82 (5H, m), 1.55 (2H, m), 1.27 (3H, m); EI-MS (m/z): 579.1 [M+H]⁺.

Example 8

(R)-{4-{4-chloro-6-[(2,4-dichlorobenzyl)amino]pyrimidin-2-yl}piperazin-1-yl}(piperidin-2-yl)methanone (Compound 8)

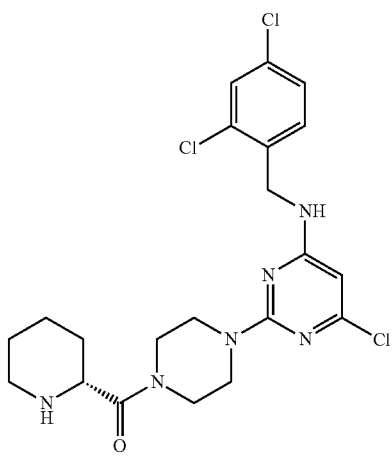 [SMILES: O=C([C@H]1CCCCN1)N1CCN(c2nc(Cl)cc(NCc3ccc(Cl)cc3Cl)n2)CC1]

Intermediate 10 (300 mg, 0.514 mmol) was dissolved in 4 mL of dichloromethane, to which 1 mL of trifluoroacetic acid was added, and stirred at room temperature for 2 hours. The reaction product was concentrated, to which 10 mL of water was added, followed by extraction 3 times with dichloromethane. The extracts were combined, washed 2 times with saturated brine, and purified through a silica gel column (eluent: ethyl acetate/methanol/ammonia), to give a white solid product.

¹H-NMR (400 MHz, DMSO) δ ppm: 9.13 (1H, s), 8.63 (1H, s), 8.08 (1H, s), 7.64 (1H, d, J=1.52 Hz), 7.27 (2H, m), 5.97 (1H, s), 4.56 (2H, d, J=4.48 Hz), 4.39 (1H, d, J=9.24 Hz), 3.76-3.22 (9H, brm), 2.87 (1H, m), 1.99 (1H, m), 1.74 (4H, m), 1.48 (1H, m); EI-MS (m/z): 483.2 [M+H]⁺.

Example 9

(R)-{4-{4-chloro-6-[(2,4-dichlorobenzyl)amino]pyrimidin-2-yl}piperazin-1-yl}(thiomorpholin-3-yl)methanone (Compound 9)

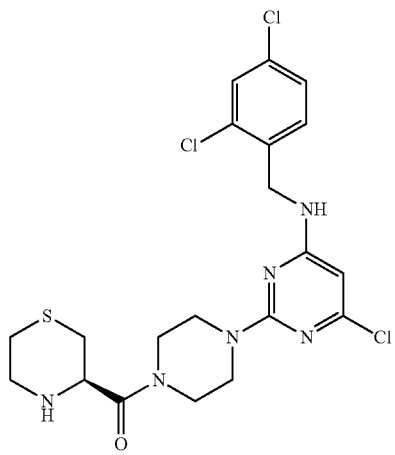 [SMILES: O=C([C@@H]1CSCCN1)N1CCN(c2nc(Cl)cc(NCc3ccc(Cl)cc3Cl)n2)CC1]

Intermediate 11 was used as raw material to go through the steps according to Example 8, to give a white solid product.

¹H-NMR (400 MHz, CDCl₃) δ ppm: 7.42 (1H, d, J=1.12 Hz), 7.27 (2H, m), 5.75 (1H, s), 5.19 (1H, s), 4.58 (2H, s), 3.95-3.44 (10H, brm), 3.12 (1H, m), 2.82 (2H, m), 2.43 (2H, m); EI-MS (m/z): 501.1 [M+H]⁺.

Example 10

1-{4-{4-[(2,4-dichlorobenzyl)amino]pyrido[2,3-d]pyrimidin-2-yl}piperazin-1-yl}propanone (Compound 10)

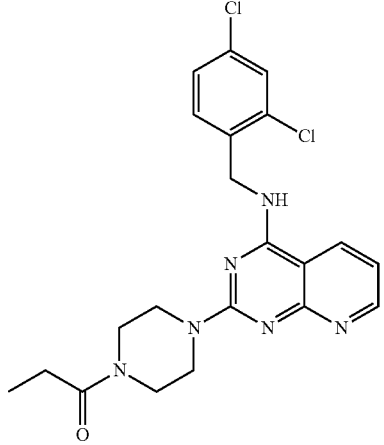 [SMILES: CCC(=O)N1CCN(c2nc(NCc3ccc(Cl)cc3Cl)c3cccnc3n2)CC1]

Intermediate 15 and propionic acid were used as raw materials to go through the steps according to Example 1, to give a white solid product.

¹H-NMR (400 MHz, CDCl₃) δ ppm: 8.76 (1H, m), 8.07 (1H, d, J=7.28 Hz), 7.42 (1H, d, J=2.24 Hz), 7.35 (1H, d, J=8.4 Hz), 7.2 (1H, m), 7.05 (1H, m), 6.61 (1H, s), 4.86 (2H, d, J=5.92 Hz), 3.97 (4H, d, J=19.32 Hz), 3.66 (2H, m), 3.50 (2H, m), 2.43 (2H, q), 1.20 (3H, t); EI-MS (m/z): 444.9 [M+H]⁺.

Example 11

1-{4-{4-[(2,4-dichlorobenzyl)amino]pyrido[2,3-d]pyrimidin-2-yl}piperazin-1-yl}-2-methylpropanone (Compound 11)

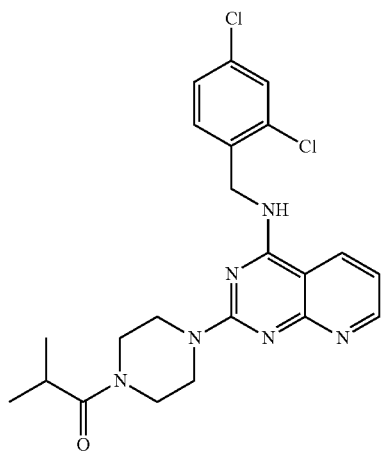 [SMILES: CC(C)C(=O)N1CCN(c2nc(NCc3ccc(Cl)cc3Cl)c3cccnc3n2)CC1]

Intermediate 15 and isobutyric acid were used as raw materials to go through the steps according to Example 1, to give a white solid product.

¹H-NMR (400 MHz, CDCl₃) δ ppm: 8.77 (1H, m), 8.02 (1H, d, J=7.56 Hz), 7.42 (1H, d, J=1.96 Hz), 7.35 (1H, d, J=8.16 Hz), 7.21 (1H, m), 7.05 (1H, m), 6.49 (1H, s), 4.86 (2H, d, J=5.6 Hz), 3.98 (4H, d, J=21.56 Hz), 3.66 (2H, m), 3.54 (2H, m), 2.86 (1H, m), 1.17 (6H, d, J=6.72 Hz); EI-MS (m/z): 459.2 [M+H]⁺.

Example 12 cyclohexyl{4-{4-[(2,4-dichlorobenzyl)amino]pyrido[2,3-d]pyrimidin-2-yl}piperazin-1-yl}methanone (Compound 12)

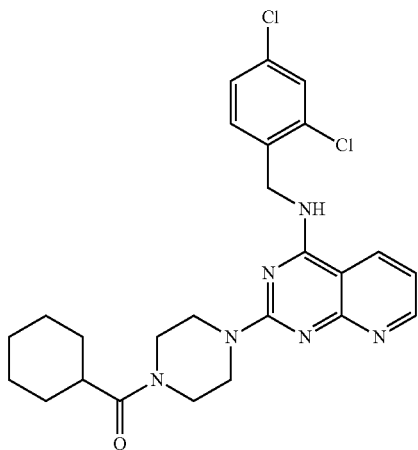 [SMILES: O=C(C1CCCCC1)N1CCN(c2nc(NCc3ccc(Cl)cc3Cl)c3cccnc3n2)CC1]

Intermediate 15 and cyclohexyl carboxylic acid were used as raw materials to go through the steps according to Example 1, to give a white solid product.

¹H-NMR (400 MHz, CDCl₃) δ ppm: 8.76 (1H, m), 8.05 (1H, d, J=7.00 Hz), 7.41 (1H, d, J=1.96 Hz), 7.35 (1H, d, J=8.12 Hz), 7.21 (1H, m), 7.04 (1H, m), 6.56 (1H, s), 4.86 (2H, d, J=5.88 Hz), 3.96 (4H, d, J=20.76 Hz), 3.65 (2H, s), 3.52 (2H, s), 2.51 (1H, m), 1.83 (5H, m), 1.52 (2H, m), 1.28 (3H, m); EI-MS (m/z): 499.1 [M+H]⁺.

Example 13

4-[(2,4-dichlorobenzyl)amino]-2-(4-propylpiperazin-1-yl)pyrido[2,3-d]pyrimidine (Compound 13)

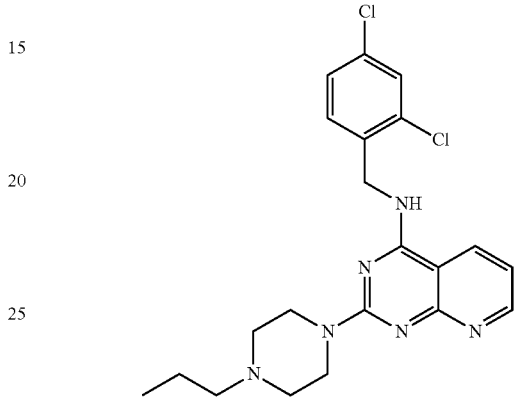

Intermediate 15 (400 mg, 1.03 mmol), 1-bromopropane (139 mg, 1.13 mmol) and DIEA (146 mg, 1.13 mmol) were dissolved in NMP (10 mL), and stirred at room temperature overnight. Thereafter, the reaction product was 5-fold diluted with ethyl acetate, washed 6 times with water, washed 3 times with saturated brine, concentrated, separated through a silica gel column (eluent: ethyl acetate/methanol/ammonia), and recrystallized with ethyl acetate, to give a white solid product.

¹H-NMR (400 MHz, CDCl₃) δ ppm: 8.74 (1H, m), 7.90 (1H, d, J=6.72 Hz), 7.41 (1H, d, J=2.24 Hz), 7.36 (1H, d, J=8.12 Hz), 7.21 (1H, m), 6.99 (1H, m), 6.18 (1H, s), 4.86 (2H, d, J=5.6 Hz), 3.97 (4H, s), 2.48 (4H, s), 2.36 (2H, t, J=7.56 Hz, J=7.84 Hz), 1.57 (2H, m), 0.95 (3H, t, J=7.28 Hz, J=7.56 Hz); EI-MS (m/z): 431.2 [M+H]⁺.

Example 14

(R)-{4-{4-[(2,4-dichlorobenzyl)amino]pyrido[2,3-d]pyrimidin-2-yl}piperazin-1-yl}(thiomorpholin-3-yl)methanone (Compound 14)

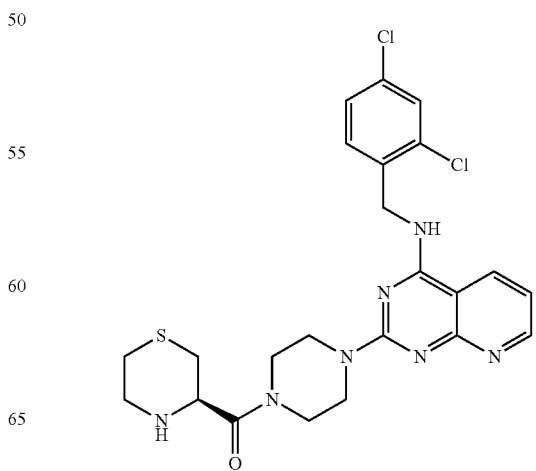

Intermediate 16 was used as raw material to go through the steps according to Example 8, to give a white solid product.

$^1$H-NMR (400 MHz, CDCl$_3$) δ ppm: 8.79 (1H, m), 7.93 (1H, dd, J=1.96 Hz, J=1.68 Hz), 7.44 (1H, d, J=1.96 Hz), 7.34 (1H, d, J=8.4 Hz), 7.22 (1H, m), 7.05 (1H, m), 6.26 (1H, t), 4.86 (2H, d, J=5.88 Hz), 4.09-3.44 (10H, brm), 3.14 (1H, m), 2.82 (2H, m), 2.44 (2H, m); EI-MS (m/z): 518.3 [H+H]$^+$.

The CCR$_4$ antagonistic activity of the compounds of the present invention can be tested by using the following method.

Example 15

Evaluation on CCR$_4$ Antagonistic Activity of the Compounds of the Present Invention Whether or not compounds 1-14 of the present invention can inhibit MDC (Peprotech) mediated chemotactic response of HEK293 cells was studied by using Boyden chamber (Neuro Probe, Inc.).

1. Construction of Receptor Expression Plasmid:

cDNA fragments including human chemokine receptor open reading frame were obtained by the following method: CCR$_4$ receptor was cloned from a cDNA library of K562 cells through polymerase chain reaction (PCR). Primers were designed according to the sequence of Gen-Bank™ accession: CCR$_4$ (NM_005508.2). cDNA fragments of receptor open reading frame were respectively inserted into pcDI (vector transformed in the chamber: eukaryotic expression vector obtained by replacing a BglII KpnI fragment of pcDNA3 (Invitrogen Corporation) plasmid with a BglII KpnI fragment of pCI (Promega Corporation) plasmid) expression vector so as to make them effectively express in HEK293 cells. DNA sequencing showed that the coding sequence was correct, and consistent with the sequence of Gen-Bank™ accession.

2. Cell Culture:

HEK293 cells were cultured in RPMI 1640 (Life Technologies, Inc.) containing 10% heat-inactivated fetal bovine serum, 100 U/mL penicillin, 100 µg/mL streptomycin. Each 4×10$^6$ HEK293 cells/400 µL were transiently transfected through electroporation with 15 µg chemokine receptor expression plasmids, under the condition of 120 V for 20 ms, the instrument used being electric pulse generator (Electro Square porator ECM 830, BTX, San Diego, Calif.). After 36-48 hr, chemotactic assay was carried out.

3. The Inhibitory Effect on MDC/TARC/C27 Mediated Chemotactic Response of HEK293 Cells Chemokines MDC/TARC/C27 were diluted to 10 ng/mL with RPMI1640 (Life Technologies, Inc.), 0.1% BSA (Sigma), and added to lower holes in a 48-hole chemotactic chamber, 27.5 µL each hole. Eukaryotic expression plasmids pCDI-CCR$_4$ were electrically shifted to HEK293 cells, and cultured normally for 36 hr. The cells were digested, resuspended with RPMI1640, 10% FBS (Life Technologies, Inc.), and subjected to rotary incubation at 37° C. for 6.5 hours. The cells were washed twice with RPMI1640, and suspended in RPMI1640, 0.1% BSA, with a final concentration of 1×10$^6$/mL. The cells and the candidate compound dissolved in DMSO (Sigma) were subjected to rotary incubation at room temperature for half an hour, the final concentration of the candidate compound being 1 µM, and the final concentration of DMSO being 0.1%, and then added to upper holes in the chemotactic chamber, 55 µL each hole. The two layers were spaced by a polycarbon membrane with pore size of 10 µM (Neuro Probe, Inc.). The chemotactic reaction was carried out in 5% CO$_2$ at 37° C. for 5 hours. There were three groups of control in the experiment, wherein the first group was positive control, in which the transfected cells were directly added to upper holes without incubated with the candidate compound, while chemokines MDC/TARC/C27 were added to lower holes. The second group was negative control, in which the transfected cells were directly added to upper holes without incubated with the candidate compound, while RPMI1640, 0.1% BSA were added to lower holes. The third group was solvent DMSO control of the candidate compound, in which the transfected cells and DMSO were incubated at room temperature, the final concentration of DMSO being 0.1%, while chemokines MDC/TARC/C27 were added to lower holes. After completion of the chemotactic reaction, the membrane was removed, fixed and stained, and, at 400× high magnification, five horizons were randomly selected to count the cells, which were then summed. The ratio of the sum of the numbers of cells in five horizons at high magnification in each experimental group to the sum of the numbers of cells in five horizons at high magnification in the negative control group is obtained as Chemotactic Index (CI). Chemotactic inhibition rate was calculated as follows:

$$100\% \times \left(1 - \frac{\text{chemotactic index of the cells co-incubated with the compound}}{\text{chemotactic index of the cells co-incubated with } DMSO}\right)$$

Compounds 1-14 of the present invention could preferably inhibit MDC/TARC/C27 mediated chemotactic response of HEK293 cells.

| Compound | MDC inhibition rate | TARC inhibition rate | C27 inhibition rate |
|---|---|---|---|
| 1 | 36.29% | 46.43% | 25.28% |
| 2 | 36.10% | 41.71% | 39.03% |
| 3 | 35.48% | 58.29% | 43.87% |
| 4 | 54.87% | 45.25% | 34.57% |
| 5 | 54.51% | 39.11% | 40.15% |
| 6 | 19.35% | 55.68% | 51.16% |
| 7 | 29.96% | 51.02% | 37.92% |
| 8 | 79.17% | 60.41% | 69.77% |
| 9 | 22.22% | 10.41% | 39.53% |
| 10 | 32.26% | 59.78% | 38.29% |
| 11 | 32.26% | 61.43% | 35.19% |
| 12 | 57.22% | 61.08% | 6.17% |
| 13 | 48.79% | 35.20% | 16.67% |
| 14 | 62.10% | 73.57% | 30.48% |

Example 16

Evaluation on the Activity of the Compounds of the Present Invention in a Mice Rhinitis Model Experiment Mice Rhinitis Model Experiment
Method:
Female BALB/c mice (6-8 weeks) were sensitized with chicken ovalbumin (OVA, Sigma-Aldrich, St Louis, Mo., USA). The compound of the present invention (for example, the compound of Example 8) was administered to nasal mucosa, at a dose 1 µg/Kg. Glucocorticoid hormonal drug budesonide, a first-line clinical drug, was used as positive control, at a dose 1.28 mg/Kg. Meanwhile, there were provided a normal group wherein the mice were not sensitized and not administered, and an OVA group wherein the mice were sensitized and not administered. The following five indicators were detected: the number of sneezing, the number of nasal scratching within 10 min after administration; IL-4 level in bronchoalveolar lavage fluid; serum IgE level; lung tissue inflammation score. Lung tissue inflammation score was rated according to a single blind method: inflammation was divided into four levels from mild to severe, marked as 0-3 scores: 0 representing no detected inflammation; 1 representing occasional inflammatory cells being visible; 2 representing bronchus or blood vessel being surrounded by eosinophils, but less than five cell layers; 3 representing bronchus or blood vessel being surrounded by a large number of eosinophils, with 5 or more cell layers.

Results:

The results were given in the table below. In terms of the number of sneezing, the Example 8 compound treatment group and the budesonide treatment group each showed a number which was significantly lower than that of the OVA-sensitized group, and slightly higher than that of the normal control group, indicating that the Example 8 compound and budesonide could significantly reduce the number of sneezing of the mice, and the effects thereof were almost the same. In terms of the number of nasal scratching, the Example 8 compound treatment group showed a number which was lower than that of any of other groups, indicating that the compound of the present invention could reduce the number of nasal scratching in the mice rhinitis model. In terms of IL-4 level in bronchoalveolar lavage fluid, the Example 8 compound treatment group and the budesonide treatment group each showed a level which was significantly lower than that of the OVA-sensitized group, and close to that of the normal control group, indicating that the compound of the present invention and budesonide could significantly reduce IL-4 level in lung of the mice, and the effects thereof were almost the same. In terms of serum IgE level, the OVA-sensitized group, the budesonide treatment group and the Example 8 compound treatment group showed quite similar levels, and all of them were higher than that of the normal control group, indicating that neither the compound of the present invention nor budesonide had an action of reducing IgE level in the mice rhinitis model. In terms of lung tissue inflammation score, the Example 8 compound treatment group and the budesonide treatment group each showed a score which was lower than that of the OVA-sensitized group, and higher than that of the normal control group, indicating that the compound of the present invention and budesonide both could reduce lung inflammation of the mice with rhinitis, and the effects thereof were close to each other.

To sum up, in the mice rhinitis model, the compound of the present invention, at a low dose (1 μg/Kg), could achieve the therapeutic effect that can be achieved by budesonide only at a high dose (1.28 mg/Kg).

TABLE 3

Effect of the Example 8 compound in the mice rhinitis model experiment

|  | Normal | OVA | Budesonide | Example 8 compound |
|---|---|---|---|---|
| Sneezing (times/10 mins) | 24.5 ± 1.8 | 51.7 ± 6.0 | 31.7 ± 4.0 | 29.0 ± 3.5 |
| Nasal scratching (times/10 mins) | 10.7 ± 0.5 | 10.5 ± 1.2 | 12.0 ± 1.3 | 8.0 ± 0.6 |

TABLE 3-continued

Effect of the Example 8 compound in the mice rhinitis model experiment

|  | Normal | OVA | Budesonide | Example 8 compound |
|---|---|---|---|---|
| IL-4(pg/mL) | 3.4 ± 0.5 | 10.1 ± 1.9 | 2.9 ± 1.5 | 3.7 ± 0.3 |
| IgE(ng/mL) | 455 ± 72 | 2853 ± 32 | 2822 ± 51 | 2861 ± 49 |
| Inflammation score | 0.8 ± 0.4 | 2.8 ± 0.4 | 1.5 ± 0.6 | 2.2 ± 0.4 |

The invention claimed is:

1. A compound of formula I,

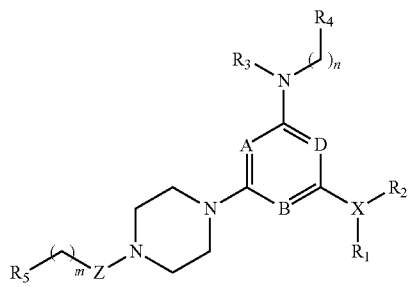

wherein:

any two of A, B and D are N and the other one is CH;

Z is selected from the group consisting of —C(O)— and —S(O)$_2$—;

X is halogen or N, with the proviso that when X is halogen, $R_1$ and $R_2$ in formula I are absent;

$R_1$ and $R_2$ are each independently selected from the group consisting of H, linear or branched alkyl having 1 to 6 carbon atoms, linear or branched heteroalkyl having 1-6 carbon atoms in which 1 to 2 of the non-terminal carbon atoms independently are replaced by O, NH, or S;

$R_3$ is H;

$R_4$ is selected from the group consisting of aryl and fused aryl containing 5 to 10 atoms; wherein said aryl or fused aryl is optionally and independently mono-, di- or poly-substituted with halogen;

$R_5$ is selected from the group consisting of linear or branched alkyl having 1 to 6 carbon atoms, linear or branched heteroalkyl having 1 to 6 carbon atoms in which 1 to 2 of the non-terminal carbon atoms independently are replaced by O, NH, or S, cycloalkyl containing 4 to 8 carbon atoms, 5- to 8-membered heterocycloalkyl containing 1 to 2 heteroatoms independently selected from the group consisting of O, N and S;

m is 0, 1 or 2; and n is 1, or a racemate or a stereoisomer, or a pharmaceutically acceptable salt or solvate thereof.

2. The compound or a racemate or a stereoisomer or a pharmaceutically acceptable salt or solvate thereof according to claim 1, wherein the aryl is selected from the group consisting of phenyl and naphthyl.

3. A compound or a racemate or a stereoisomer or a pharmaceutically acceptable salt or solvate thereof, wherein the compound is selected from the group consisting of:

1-{4-{4-[(2,4-dichlorobenzyl)amino]-6-[(2,2-dimethoxyethyl)methylamino]pyrimidin-2-yl}piperazin-1-yl}propanone;

1-{4-{4-[(2,4-dichlorobenzyl)amino]-6-[(2,2-dimethoxyethyl)methylamino]pyrimidin-2-yl}piperazin-1-yl}-2-methylpropanone;

1-{4-{4-[(2,4-dichlorobenzyl)amino]-6-[(2,2-dimethoxyethyl)methylamino]pyrimidin-2-yl}piperazin-1-yl}-3-methylthiopropanone;

1-{4-{4-[bis(2-methoxyethyl)amino]-6-(2,4-dichlorobenzylamino)-pyrimidin-2-yl}piperazin-1-yl}propanone;

1-{4-{4-[bis(2-methoxyethyl)amino]-6-(2,4-dichlorobenzylamino)-pyrimidin-2-yl}piperazin-1-yl}-2-methylpropanone;

1-{4-{4-[bis(2-methoxyethyl)amino]-6-(2,4-dichlorobenzylamino)-pyrimidin-2-yl}piperazin-1-yl}-3-methylthiopropanone;

4-{4-[bis(2-methoxyethyl)amino]-6-(2,4-dichlorobenzylamino)-pyrimidin-2-yl}piperazin-1-yl}cyclohexylmethanone;

(R)-{4-{4-chloro-6-[(2,4-dichlorobenzyl)amino]pyrimidin-2-yl}piperazin-1-yl}(piperidin-2-yl)methanone; and (R)-{4-{4-chloro-6-[(2,4-dichlorobenzyl)amino]pyrimidin-2-yl}piperazin-1-yl}(thiomorpholin-3-yl)methanone.

4. A pharmaceutical composition comprising the compound of formula I or a racemate or a stereoisomer or a pharmaceutically acceptable salt or solvate thereof according to claim 1, and at least one pharmaceutically acceptable carrier, diluent or excipient.

5. A method of treating a chemokine receptor 4 (CCR4)-related disease or disorder selected from the group consisting of allergic rhinitis, asthma and allergic dermatitis, the method comprising administering a therapeutically or prophylactically effective amount of the compound of formula I or a racemate or a stereoisomer or a pharmaceutically acceptable salt or solvate thereof according to any one of claims 1 to 3 to a subject in need thereof.

6. A pharmaceutical composition comprising (R)-{4-{4-chloro-6-[(2,4-dichlorobenzyl)amino]pyrimidin-2-yl}piperazin-1-yl}(piperidin-2-yl)methanone, or a racemate or a stereoisomer or a pharmaceutically acceptable salt or solvate thereof, and at least one pharmaceutically acceptable carrier, diluent or excipient.

7. (R)-{4-{4-chloro-6-[(2,4-dichlorobenzyl)amino]pyrimidin-2-yl}piperazin-1-yl}(piperidin-2-yl)methanone.

8. The method of claim 5, wherein the compound is (R)-{4-{4-chloro-6-[(2,4-dichlorobenzyl)amino]pyrimidin-2-yl}piperazin-1-yl}(piperidin-2-yl)methanone.

9. The compound of claim 1, in which 1 to 2 of the non-terminal carbon atoms of the linear or branched heteroalkyl independently are replaced by O or S.

* * * * *